United States Patent
Rehwald

(10) Patent No.: US 11,119,176 B2
(45) Date of Patent: Sep. 14, 2021

(54) AUTOMATIC CAPTURE OF CARDIAC MOTION BY PRE-SCAN AND AUTOMATED DATA EVALUATION FOR DETERMINATION OF MOTIONLESS PERIODS WITHIN THE RR-INTERVAL

(71) Applicant: Siemens Healthcare GmbH, Erlangen (DE)

(72) Inventor: Wolfgang G. Rehwald, Chapel Hill, NC (US)

(73) Assignee: Siemens Healthcare GmbH, Erlangen (DE)

( * ) Notice: Subject to any disclaimer, the term of this patent is extended or adjusted under 35 U.S.C. 154(b) by 962 days.

(21) Appl. No.: 15/822,565

(22) Filed: Nov. 27, 2017

(65) Prior Publication Data

US 2019/0162808 A1    May 30, 2019

(51) Int. Cl.
| | |
|---|---|
| *G01R 33/56* | (2006.01) |
| *A61B 5/00* | (2006.01) |
| *G01R 33/567* | (2006.01) |
| *G01R 33/563* | (2006.01) |
| *A61B 90/00* | (2016.01) |

(Continued)

(52) U.S. Cl.
CPC ........ *G01R 33/5673* (2013.01); *A61B 5/0044* (2013.01); *A61B 5/7285* (2013.01); *G01R 33/5676* (2013.01); *G01R 33/56325* (2013.01); *A61B 5/055* (2013.01);
(Continued)

(58) Field of Classification Search
CPC .......... G01R 33/5673; G01R 33/56325; G01R 33/5676; G01R 33/546; G01R 33/56509; G01R 33/5608; A61B 5/7285; A61B 5/0044; A61B 2090/374; A61B 5/055; A61B 5/725
See application file for complete search history.

(56) References Cited

U.S. PATENT DOCUMENTS

| | | |
|---|---|---|
| 5,766,128 A | 1/1998 | Halamek et al. |
| 6,516,210 B1 | 2/2003 | Foxall |

(Continued)

OTHER PUBLICATIONS

C. Stehning et al. Free-Breathing Whole-Heart Coronary MRA With 3D Radial SSFP and Self-Navigated Image Reconstruction; Magnetic Resonance in Medicine 54:476-480 (2005).

(Continued)

*Primary Examiner* — Christopher Koharski
*Assistant Examiner* — Katherine M Mcdonald

(57) ABSTRACT

A method for determining time periods of minimal motion of a physiologic organ includes monitoring a physiologic triggering signal associated with a patient and using an MRI cine pulse sequence to acquire a temporal series of projections of the organ. The temporal series is analyzed to determine times relative to a physiologic triggering signal during which motion of the organ is below a threshold. Motion is assessed by first creating a signal intensity versus time curve of one pixel or an average of multiple pixels included in the temporal series. A noise filter and normalization is applied to the signal intensity versus time curve to yield a filtered and normalized time curve. The temporal derivative of the filtered and normalized time curve is determined. The absolute value of the motion-analog function is evaluated for being smaller than the threshold to determine the times where motion is below the threshold.

22 Claims, 28 Drawing Sheets

Patient Example 1: All 28 Individual Cardiac Phases of a Typical Cine MRI Acquisition

(51) Int. Cl.
*A61B 5/055* (2006.01)
*G01R 33/54* (2006.01)
*G01R 33/565* (2006.01)

(52) U.S. Cl.
CPC ...... *A61B 2090/374* (2016.02); *G01R 33/546* (2013.01); *G01R 33/5608* (2013.01); *G01R 33/56509* (2013.01)

(56) References Cited

U.S. PATENT DOCUMENTS

| 6,798,199 B2 | 9/2004 | Larson et al. | |
|---|---|---|---|
| 2011/0178392 A1* | 7/2011 | Kuhara | G01R 33/56509 600/413 |
| 2012/0194187 A1* | 8/2012 | Rehwald | G01R 33/563 324/309 |

OTHER PUBLICATIONS

Kim, W.S., et al., Extraction of cardiac and respiratory motion cycles by use of projection data and its applications to NMR imaging. Magn Reson Med, 1990. 13(1): p. 25-37.

Kim, W.S. and Z.H. Cho, Cardiac cycle extraction from projection data using static signal suppression. Magnetic Resonance in Medicine, 1992. 24(1): p. 182-188.

Spraggins, T.A., Wireless retrospective gating: application to cine cardiac imaging; Magn Reson Imaging, 1990. 8(6): p. 675-681.

Larson, A.C., et al., Self-gated cardiac cine MRI. Magn Reson Med, 2004. 51(1): p. 93-102.

Crowe, M.E., et al., Automated rectilinear self-gated cardiac cine imaging. Magn Reson Med, 2004. 52(4): p. 782-8.

Liu, J., et al., Self-gated free-breathing 3D coronary CINE imaging with simultaneous water and fat visualization. PLoS One, 2014. 9(2): p. e89315.

* cited by examiner

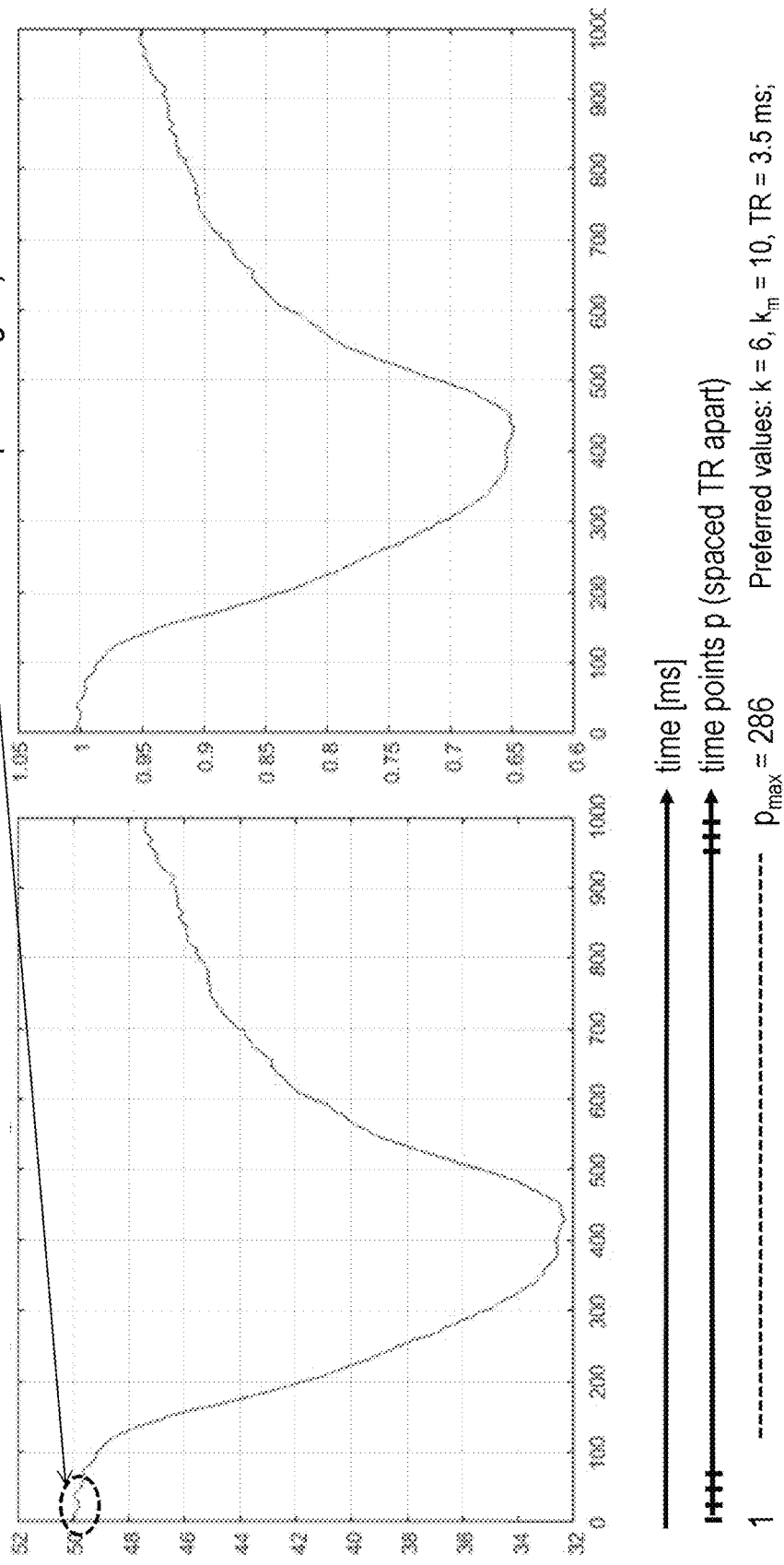

Smoothing Data By Sliding Time Window Averaging (A) and Normalizing (B)

*FIG. 8A*: Signal intensity $\bar{S}$ from FIG. 7B averaged across k time points (sliding window)

*FIG. 8B*: Signal of FIG. 7A normalized to the average of the first $k_m$ data points (inside elliptical region)

Preferred values: $k = 6$, $k_m = 10$, TR = 3.5 ms;
$p_{max}$ is proportional to the RR interval and is about RR/TR, in this example
RR/TR = 1000 ms / 3.5 ms ≈ 286 points

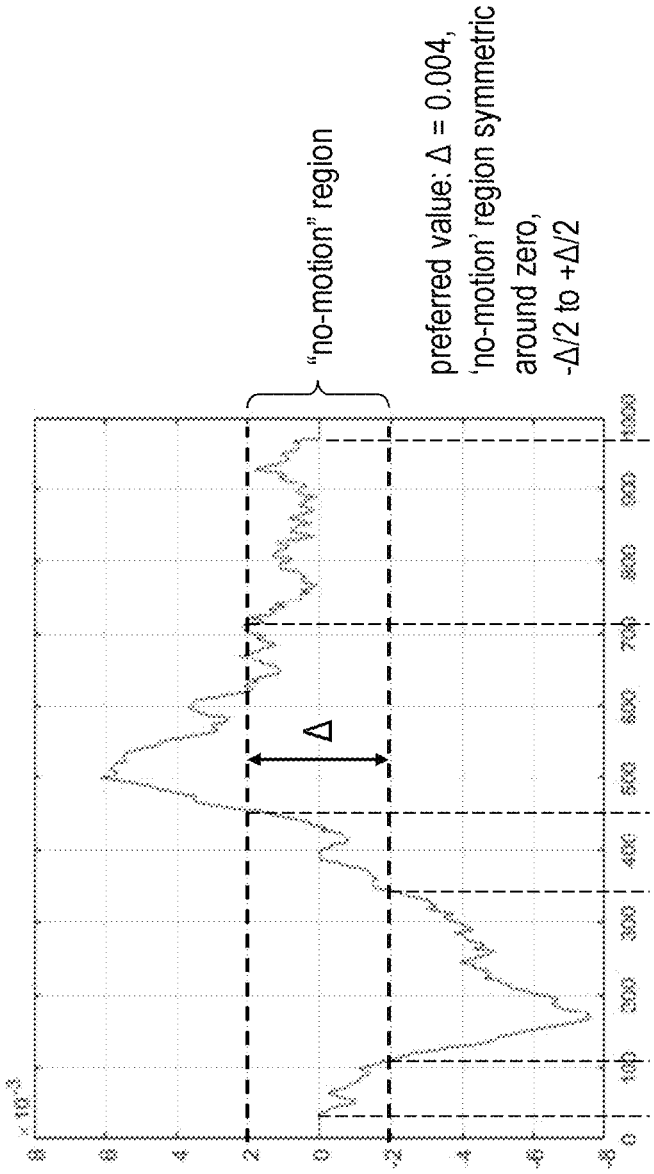
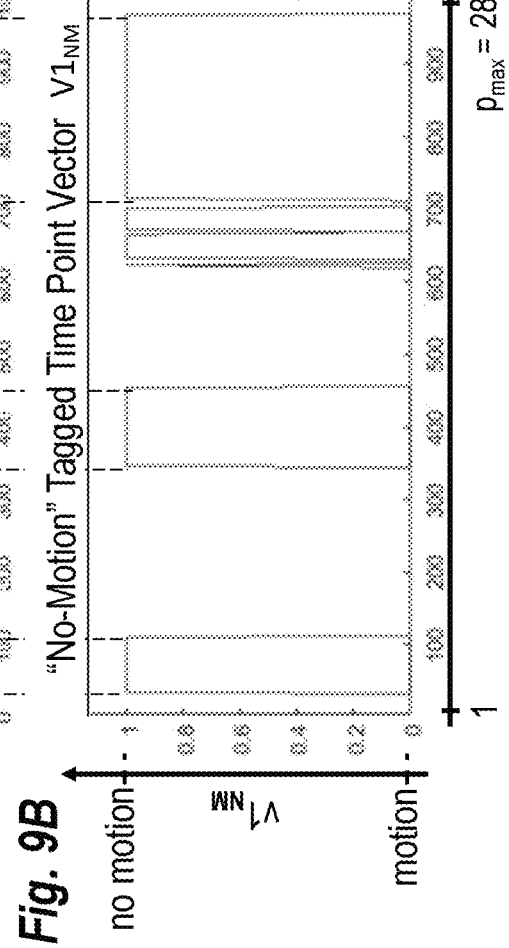
Fig. 9A
Fig. 9B

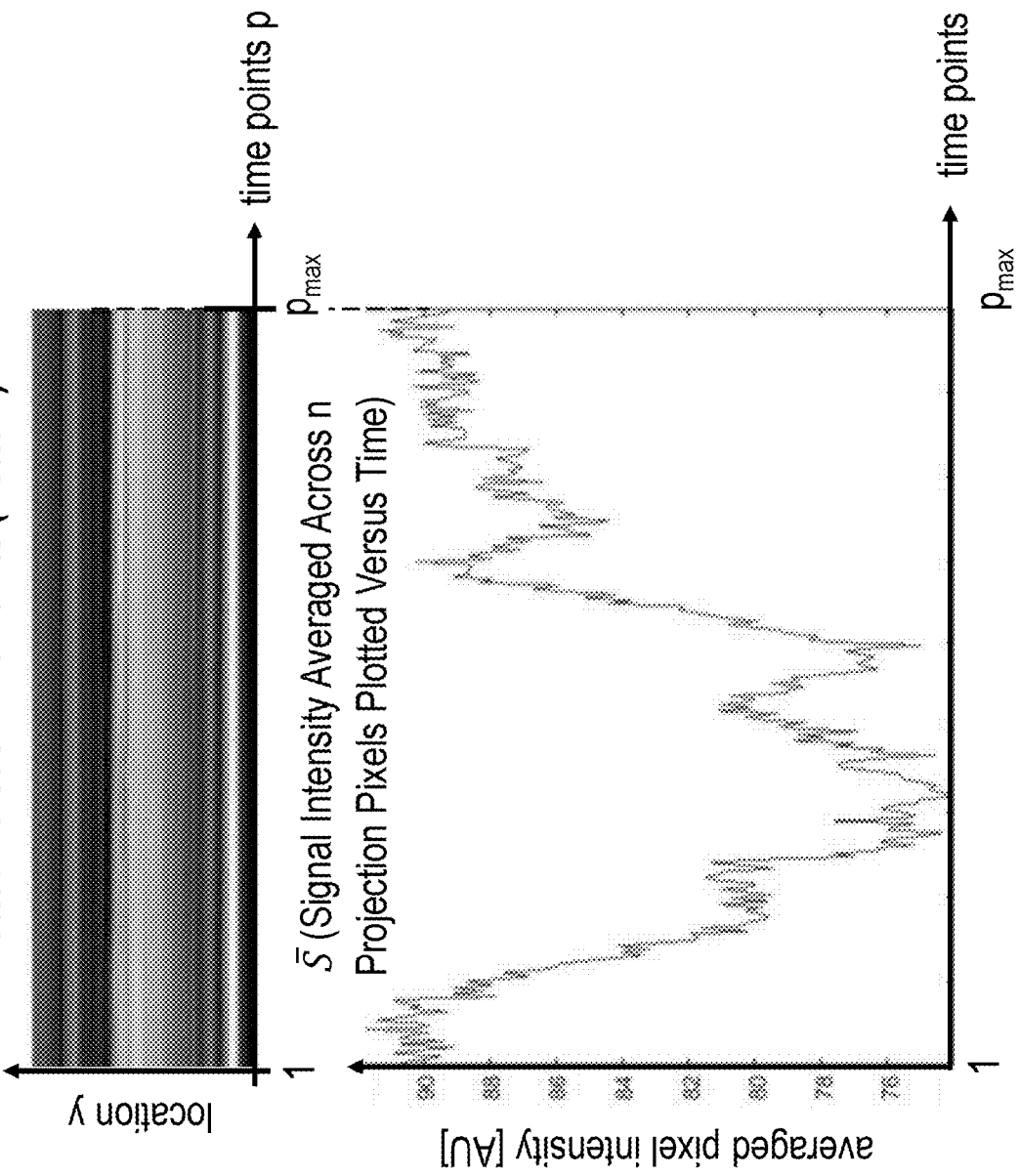
Fig. 14A / Fig. 14B. Data from Patient 2: All Projection Pixels Versus Time Points (Top) and the Average Pixel Intensity of the n Projection Pixels with the Largest Difference Across Time Points Plotted Versus Time Points (Bottom)

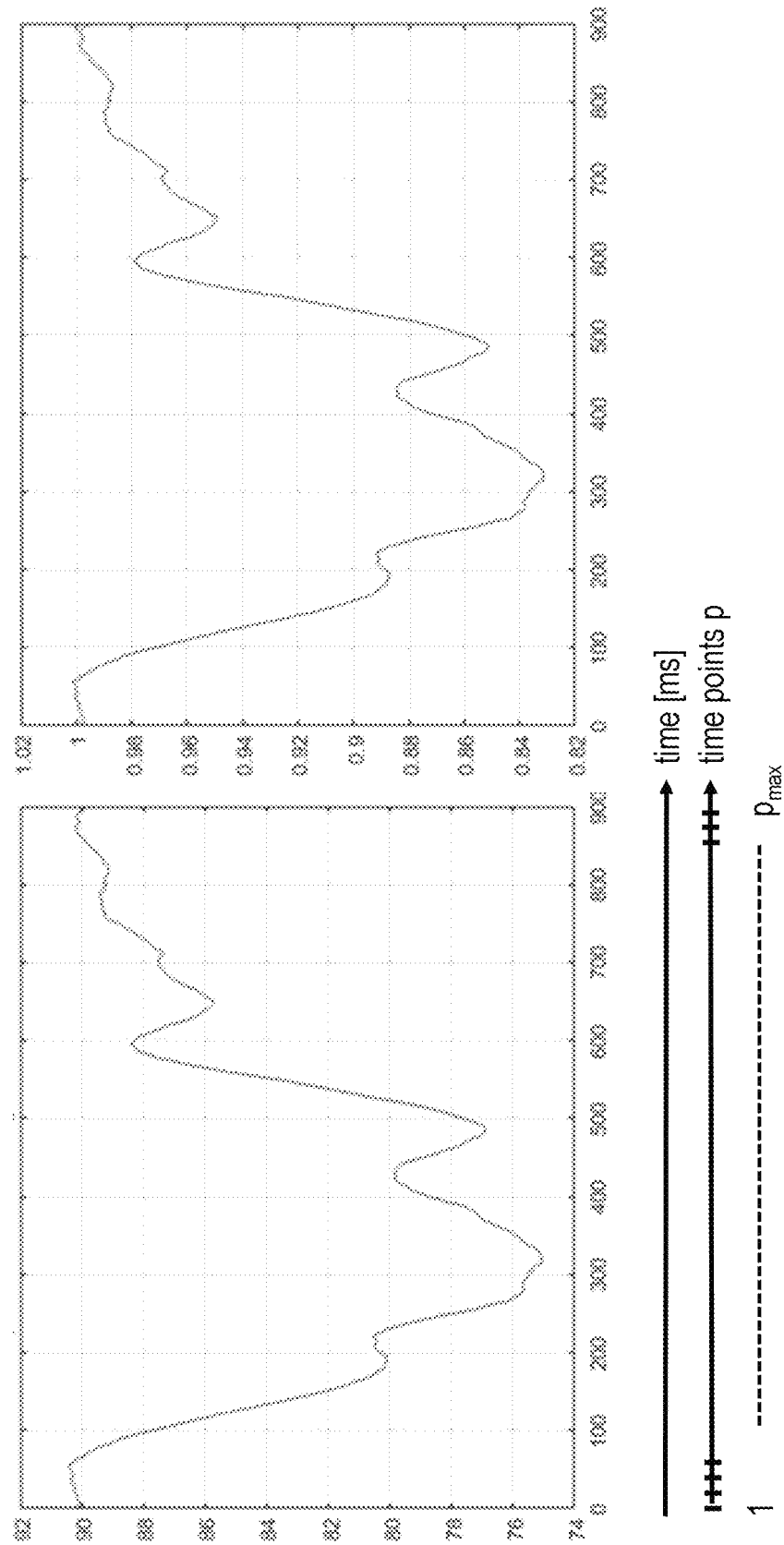
Fig. 15A: Signal intensity $\bar{S}$ from Fig. 14B averaged across k time
Fig. 15B: Signal of Fig. 15A normalized to the average of the first $k_m$ data points

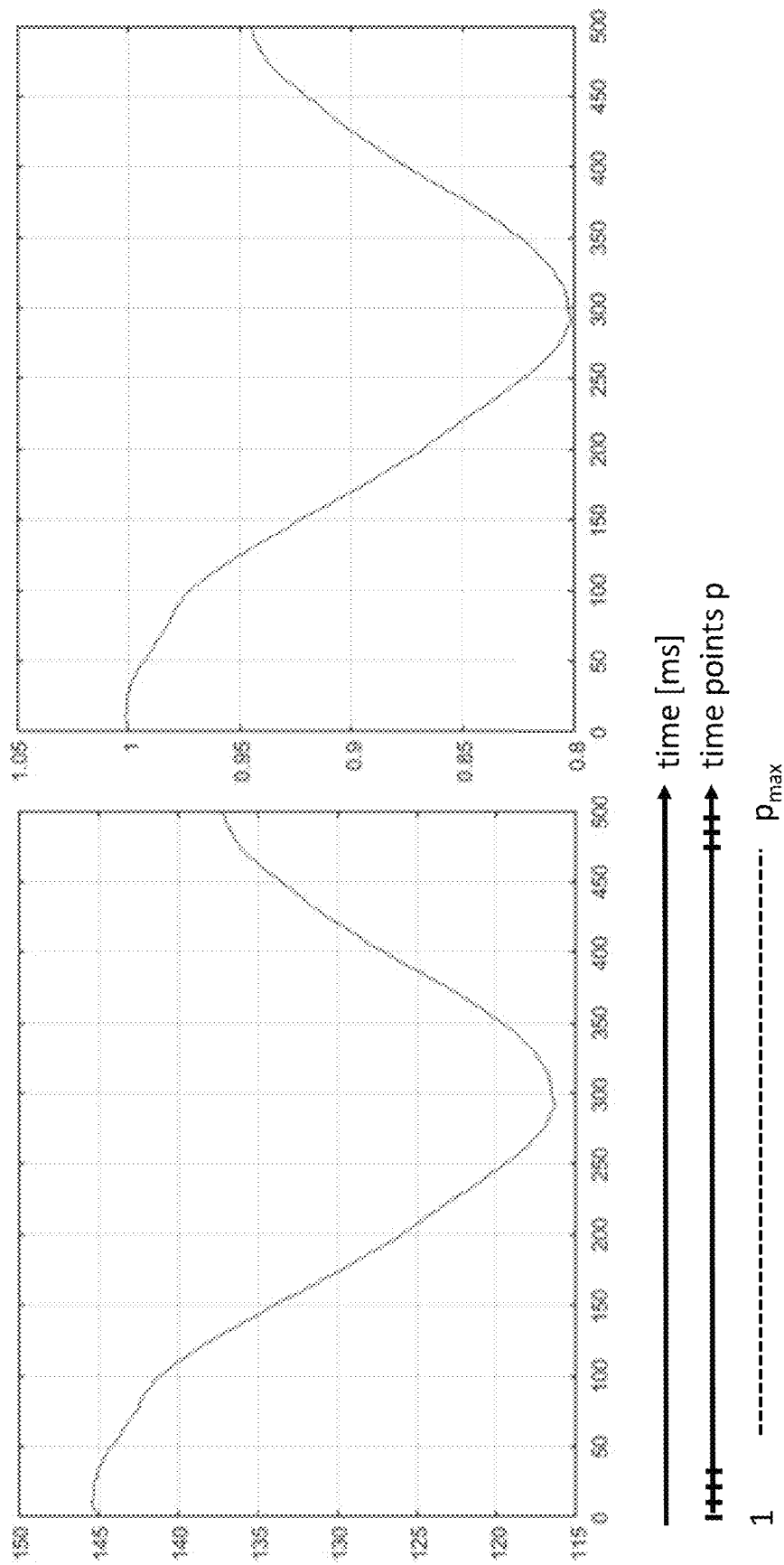

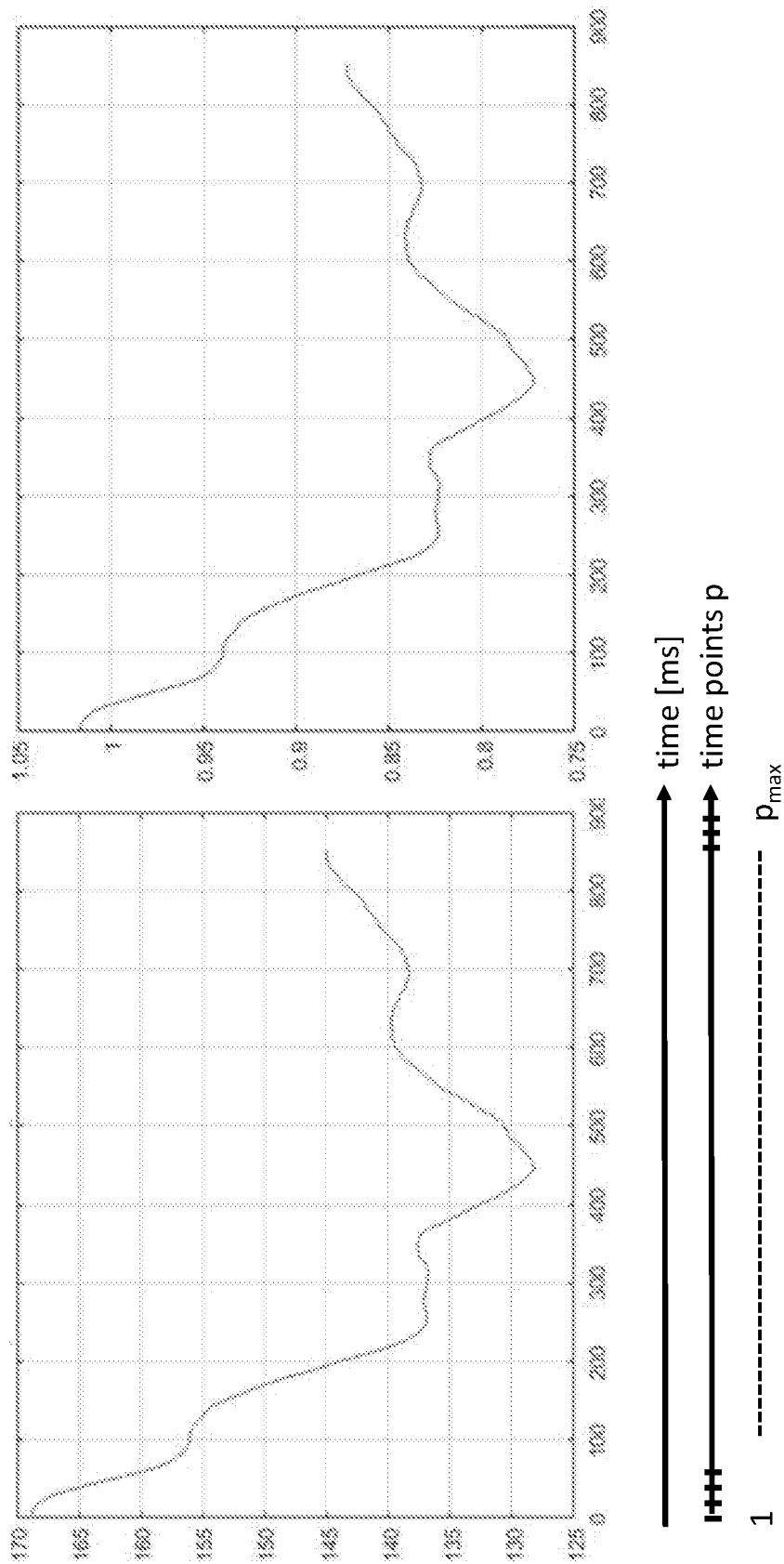
Smoothing Data By Sliding Time Window Averaging (A) and Normalizing (B)
*Fig. 25A*: Signal intensity $\bar{S}$ from Fig. 24A averaged across k time
*Fig. 25B*: Signal of Fig. 25A normalized to the average of the first $k_m$ data points Derivative of FIG. 25B

AUTOMATIC CAPTURE OF CARDIAC MOTION BY PRE-SCAN AND AUTOMATED DATA EVALUATION FOR DETERMINATION OF MOTIONLESS PERIODS WITHIN THE RR-INTERVAL

TECHNOLOGY FIELD

The present invention relates to methods, systems, and apparatuses for Magnetic Resonance Imaging (MRI) in general and the assessment of cardiac motion in particular, specifically the detection of time periods within the cardiac cycle that exhibit no or minimal cardiac motion.

BACKGROUND

The heart beats in a periodic manner with its period called RR-interval. 'R' stands for the R-wave which is observable in an electrocardiogram (ECG) and indicates the electrical activity initiating the heart's contraction as beginning of the cardiac cycle. The cardiac cycle lasts from one R-wave to the next and its duration or period is hence called RR-interval.

Two time windows typically exist within the RR-interval during which the heart shows no or minimal cardiac motion. The first time window occurs during isovolumetric relaxation at the end of systole. It has a relatively short duration of about 70 ms (to some degree RR-dependent) and falls between the closure of the aortic valve and the opening of the mitral valve. Even though the aortic valve closure marks the beginning of diastole, imaging during this window is termed "systolic imaging" in the Magnetic Resonance (MR) community due to the proximity to systole. The second time window occurs during a fraction of diastole known as diastasis. Its duration depends on the length of the RR-interval. For high heart rates (short RR-interval) there generally exists no diastolic time window without motion.

The absence of motion during data acquisition by MRI is very important as many types of acquisition (also called readout) are very sensitive to motion and flow. Specifically the turbo-spin echo (TSE) readout is prone to this problem. Manifestations of this sensitivity include signal dropout increasing with motion, signal inhomogeneity of the myocardium wherein increased local motion causes reduced local signal, and fuzziness of the acquired image (reduced effective spatial resolution similar to camera shake in photography).

Scanner operators equipped with experience, sufficient time, and knowledge of the heart would acquire a cine series (a movie) of the beating heart at the slice location to be imaged with the TSE sequence. They would then manually set the timing parameters of the TSE sequence (start and end of the TSE readout) to limit the acquisition to the no-motion time window, generally during part of diastole. Because this window can change in the same patient during the same exam, for example due to stress or repeated breath holding, the cine series would need to be acquired repeatedly for every imaged slice. Additionally, the no-motion window occurs at somewhat different times for different locations (e.g., a basal slice depicting the atria compared to a mid-ventricular slice showing the ventricles). Thus each slice location would ideally require its own cine series for optimal timing determination and would need to be acquired immediately before the TSE sequence. Knowing that the acquisition of a cine series takes a ten-second breath hold it is obvious that no scanner operator would stick to such a cumbersome procedure. In most imaging centers the situation is even worse. Many operators place the time window by a vendor provided logic (for example "capture-cycle" logic) that only accounts for the RR duration, but not for the individual patient's heart morphology, disease, and acquired location. The resulting image quality is frequently poor to non-diagnostic.

The most common method for selecting a minimal or no-motion time window is a vendor-provided logic, for example, called "capture-cycle" logic. With the push of a button it allows the scanner operator to set the end time of sequence readout to a supposed no-motion window. It has multiple issues. It does not set the start time of the readout, just the end time. Therefore it does not adjust the duration of the readout window even though it is known that the no-motion period varies with the RR duration and by patient. But its main problem is that it acts on the RR duration alone and does not account for the individual patient's cardiac morphology, heart disease, and the location to be acquired (e.g., base, apex, outflow tract), because this information is not available to this method. Instead it derives the end time from the RR alone and its algorithm is based on the RR of normal volunteers. The resulting image quality is frequently poor to non-diagnostic, especially in patients with cardiac disease, which represent the majority of scanned subjects.

Another method for selecting a minimal or no-motion time window is more precise, because it is patient-specific. However, it is time consuming and requires expert skill of the scanner operator. Therefore it is rarely used by research sites and hardly ever used by standard clinical sites. In this method a scanner operator acquires a movie of the beating heart (also called a cine series) at the slice location to be imaged with the motion sensitive use-sequence. He then pages through the series of acquired movie frames, (cardiac phases) to find start and end time of the no-motion window. This is possible as the frames have time stamps relative to the preceding R-wave or other trigger signal. Then the operator manually sets the timing parameters of the use-sequence. In the TSE sequence for example, the operator sets the end time of the TSE readout and the turbo factor to adjust the readout length, which indirectly sets the start time. Setting the times for the use-sequence is only as precise as the temporal resolution of the cine frames, which is typically 40-60 ms. The readout time window of the use-sequence may thus not fully utilize the entire no-motion period as it is only known to the limits of the movie's temporal resolution.

Because the no-motion window can change in the same patient during the same exam (e.g., due to stress or repeated breath holding) the cine series needs to be acquired repeatedly for every imaged slice. Additionally, the no-motion window occurs at somewhat different times for a basal slice depicting the atria and a mid-ventricular slice showing the ventricles. Thus, each slice location would ideally require its own cine series for optimal timing determination and would need to be acquired immediately before the use-sequence. As the acquisition of a cine-series takes about a ten-second breath hold, no scanner operator would acquire the cine-series as often as required in the above described ideal procedure, even if the operator is familiar with it and capable of applying it. Suboptimal image quality may result.

SUMMARY

Embodiments of the present invention address and overcome one or more of the above shortcomings and drawbacks, by providing methods, systems, and apparatuses related to an automatic capture of cardiac motion by pre-scan and automated data evaluation for determination of motionless periods within the RR-interval. Briefly, the motion assessment technique described herein represents a fully automatic method for acquiring data on motion of a patient's heart by a pre-scan, determining the motionless periods within the cardiac cycle from that data, and setting the timing parameters of a consecutively run use-sequence such as a Turbo Spin Echo (TSE) sequence so that its readout occurs during the motionless period.

According to some embodiments, the motion assessment technique described herein comprises a two-heart beats pre-scan to determine the patient's cardiac motion. Following the pre-scan, the acquired data is analyzed and the number of motionless periods within the RR-interval is output, along with their respective start and end times relative to the preceding R-wave or other trigger signal. In case of high heart rates, the technique described herein typically finds a single time window for systolic imaging. In case of normal or low heart rates it usually finds two windows, one for systolic and one for diastolic imaging. A predefined user preference of diastolic or systolic imaging allows the motion assessment technique to provide exactly one no-motion window to the following "use-sequence" (TSE or other motion-sensitive sequence) by furnishing one set of readout start and end time.

According to some embodiments, a method for determining time periods of minimal motion of a physiologic organ relative to a trigger of a physiologic triggering signal and within a triggering cycle includes monitoring the physiologic triggering signal associated with a patient and using an MRI cine pulse sequence to acquire a temporal series of projections across a region of interest comprising an organ of interest. The temporal series of projections are analyzed to determine one or more times relative to a trigger provided by the physiologic triggering signal during which motion of the organ of interest is below a predefined threshold. Motion of the organ of interest is assessed by first creating a signal intensity versus time curve of one pixel or an average of multiple pixels included in the temporal series of projections. A noise filter and normalization is applied to the signal intensity versus time curve to yield a filtered and normalized time curve. The temporal derivative of the filtered and normalized time curve is determined to yield a motion-analog function. Then, the absolute value of the motion-analog function is evaluated for being smaller than the predefined threshold to determine the one or more times.

Various enhancements, refinements, and other modifications can be made in different embodiments of the present invention. For example, in some embodiments, the projections are repeatedly acquired at same locations at consecutive times during at least 90% of one triggering cycle. In another embodiment, the signal intensity versus time curve is an average of a plurality of pixels in the series of projections across all time points. In other embodiments, the motion-analog function is averaged across time with sliding window averaging in which a sliding window is applied to a number of consecutive elements and is moved along entire the motion-analog function.

In some embodiments of the aforementioned method, elements for which an absolute value of the derivative is below a predefined threshold are tagged as having no motion in a tag-vector comprising a same number of elements as a motion-analog function. A sliding median filter may be applied to the tag-vector and moved along the entire tag-vector creating a median-filtered tag-vector. The median-filtered tag-vector may be further filtered replacing its no-motion tagged regions that are shorter than a minimum duration by motion tagged regions. In one embodiment, this minimum duration depends on duration of the triggering cycle. The method may further include calculating a number of no-motion regions and their respective start and end times from the tag-vector and saving the number of no-motion regions and their respective start and end times as timing data.

According to another aspect of the present invention, an article of manufacture for determining time periods of minimal motion of a physiologic organ relative to a trigger of a physiologic triggering signal and within a triggering cycle comprises a computer-readable, non-transitory medium holding computer-executable instructions for performing the aforementioned method. These instructions may further be refined based on any of the modifications of the aforementioned method discussed above.

According to other embodiments of the present invention, a system for determining time periods of minimal motion of a physiologic organ relative to a trigger of a physiologic triggering signal and within a triggering cycle include a physiologic monitoring device, an MRI scanner, and a data processor. The physiologic monitoring device is configured to monitor the physiologic triggering signal associated with a patient. The MRI scanner is configured to use an MRI cine pulse sequence to acquire a temporal series of projections across a region of interest comprising an organ of interest. The data processor analyzes the temporal series of projections to determine one or more times relative to a trigger provided by the physiologic triggering signal during which motion of the organ of interest is below a predefined threshold. Motion of the organ of interest is assessed by a process comprising: (a) creating a signal intensity versus time curve of one pixel or an average of multiple pixels included in the temporal series of projections, (b) applying a noise filter and normalization to the signal intensity versus time curve to yield a filtered and normalized time curve, (c) determining the temporal derivative of the filtered and normalized time curve to yield a motion-analog function, and (d) evaluating the absolute value of the motion-analog function for being smaller than the predefined threshold to determine the one or more times.

Additional features and advantages of the motion assessment technique will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the motion assessment technique, there is shown in the drawings embodiments that are presently preferred, it being understood, however, that the motion assessment technique is not limited to the specific instrumentalities disclosed. Included in the drawings are the following Figures:

FIG. 8A shows the result of temporal filtering of the curve from FIG. 7B by a sliding window average filter;

FIG. 8B shows a normalized version of the curve shown in FIG. 8A;

FIG. 9A shows the derivative of the normalized curve of FIG. 8B;

FIG. 9B shows a vector $V1_{NM}(p)$ which has each time point tagged as possessing cardiac motion or not;

FIG. 14A depicts a magnification of the first (upper left) and the last panel of FIG. 13, showing all projection pixels versus time points for a second patient;

FIG. 14B shows average pixel intensity of the n projection pixels with the largest difference across time points plotted versus time points for a second patient for the data shown in FIG. 14A;

FIG. 15A shows the result of temporal filtering of the curve from FIG. 14B by a sliding window average filter;

FIG. 15B shows a normalized version of the curve shown in FIG. 15A;

FIG. 20A shows the result of temporal filtering of the curve from FIG. 19B by a sliding window average filter;

FIG. 20B shows a normalized version of the curve shown in FIG. 20A;

FIG. 25A shows the result of temporal filtering of the curve from FIG. 24B by a sliding window average filter;

FIG. 25B shows a normalized version of the curve shown in FIG. 25A;

DETAILED DESCRIPTION OF ILLUSTRATIVE EMBODIMENTS

Figure 1:
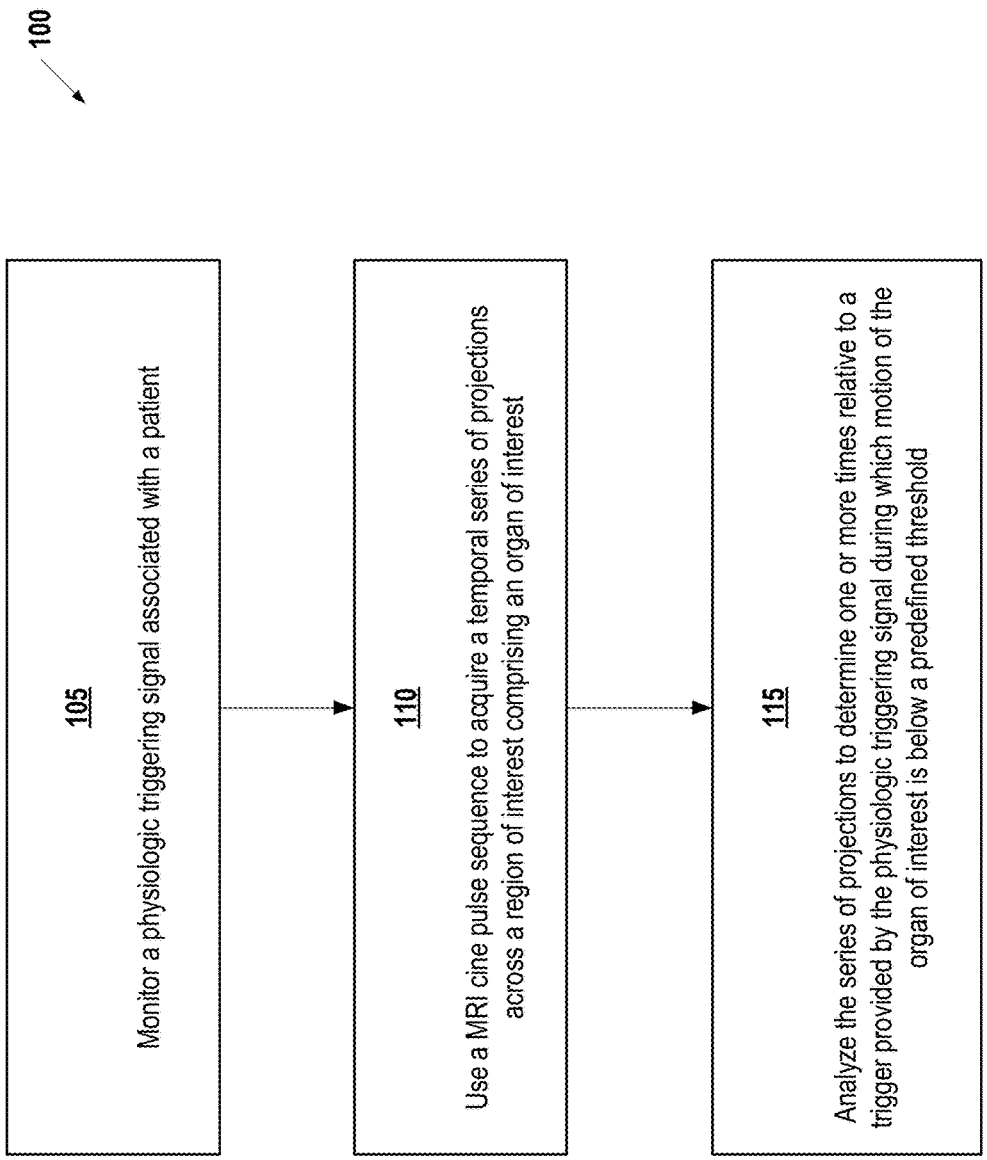
FIG. 1 shows a flowchart illustrating a high-level overview of a method for determining time periods of minimal motion of a physiologic organ such as the heart, according to some embodiments of the present invention.

The following disclosure describes the present invention according to several embodiments directed at methods, systems, and apparatuses related to the automatic capture of cardiac motion by pre-scan and automated data evaluation for determination of motionless periods within the RR-interval. The motion assessment technique described herein has the function to measure cardiac motion in a slice location to be acquired with a use-sequence and then provide a time window of minimal or no motion to the use-sequence, so that the latter can acquire data during the part of the cardiac cycle with minimal or no motion. The function is realized by combining a data acquisition with a data processing part executed in rapid succession. Data analysis takes at the most one RR-interval so that the motion assessment technique requires only two or three RR-intervals in total. One important aspect of the motion assessment technique is that it delivers precision in regards to best timing of the readout to a no-motion window, without the traditionally required significant time effort and knowledge. This is a major improvement over existing precise yet time consuming methods and over other existing quick yet imprecise methods.

The main problem of the capture-cycle logic is that it is solely based on the RR-interval and assumes a normal healthy heart. The motion assessment technique described herein overcomes this significant limitation by collecting patient-specific data, acquired immediately before the use-sequence in the location to be imaged. Therefore it accounts for any disease-specific deviations from the normal heart, for location-specific timing, and for cardiac timing behavior varying over the duration of an MR exam. The combined pre-scan and data analysis is tailored exactly to disease-, location-, and time-specific properties of the patient's heart to be imaged. Manual placement of the time window is problematic in that it takes too long and requires the expertise and willingness of the scanner operator to execute it. These requirements are usually not met. Therefore the method is hardly used even though in principle it can find the no-motion period and improve image quality. The technology described herein solves the problems of both existing methods by determining the timing specifically for the imaged heart and location, while requiring no manual operator intervention and only minimal time.

Technical details of the motion assessment technique may be summarized as follows. The pre-scan component is a modified cine sequence. Unlike conventional cine sequences, the motion assessment technique described herein acquires only the central line of the raw data (k-space) by not using a phase encoding gradient. It acquires the same line every time-to-repeat (TR) which is typically between 2.5 and 5 ms long, throughout one cardiac cycle. The resulting projection image has exactly one line that is spatially resolved in frequency encoding direction and not resolved in phase-encoding direction. The motion assessment technique provides excellent temporal resolution that equals TR. Approximately one heartbeat of data is acquired, which equals "RR-interval divided by TR" time points, between 150 and 300 points.

FIG. 1 shows a flowchart illustrating a high-level overview of a method 100 for determining time periods of minimal motion of a physiologic organ such as the heart, according to some embodiments of the present invention. These time periods are determined relative to a trigger of a physiologic triggering signal.

This method 100 shown in FIG. 1 can be initiated in a variety of ways. For example, in some embodiments, the method is an executable application that is automatically executed when the command to run the use-sequence is issued by the scanner operator. In this case, the pre-scan (also known as adjustment scan), data analysis, and furnishing of start and end times to the use-sequence is done on the fly immediately before running the use-sequence. To the operator, pre-scan and use-sequence appear as single event and both are executed during one breath-hold without noticeable delay between them. The advantage of this implementation is that motion assessment technique and use-sequence are run within the same breath-hold. In many patients breath-holding changes a patient's RR-interval. Both consistently shorter and longer RR durations have been observed. Therefore, it is advantageous to assess the motion and acquire the use-data in the same breath-hold. In another implementation the execution of the method 100 is initiated by pressing a button on the scanner's graphical user interface (GUI) or other user interface. This button is often called "capture cycle". The button is on the user interface card of the use-sequence and modifies its timing parameters. Pressing an "apply" or "run" button after pressing the "capture cycle" button will run the use-sequence using the timing information provided by the method 100.

Starting at step 105, a physiologic triggering signal associated with a patient is monitored over a plurality of triggering cycles. Each triggering cycle may be, for example, an RR-interval. Examples of physiologic triggering signals that may be monitored at step 105 include an electrocardiogram, a pulse oximetry signal, an acoustic heart signal, or a respiratory signal. Next at step 110, an MRI cine pulse sequence is used to acquire a series of projections across a region of interest comprising an organ of interest. The MRI cine pulse sequence may be prospectively triggered or retrospectively gated with respect to the physiologic triggering signal. Various types of MRI cine pulse sequences may be used at step 110. For example, in some embodiments, the MRI cine pulse sequence is a steady state free precession (SSFP) sequence. In other embodiments, the MRI cine pulse sequence is a gradient echo (GRE) sequence. In some embodiments, the MRI cine pulse sequence repeatedly acquires the projections at the same locations for consecutive times during at least 90% of one triggering cycle.

Continuing with reference to FIG. 1, at step 115, the temporal series of projections is analyzed to determine one or more times relative to a trigger provided by the physiologic triggering signal during which the absolute value of the velocity associated with motion of the organ of interest is below a predefined threshold. To produce said velocity as a function of time, in a first step the pixel signal intensity at one location on the line of projection pixels is plotted as function of time relative to said trigger. In some embodiments, a plurality of pixels in each projection may be averaged together, and this average is plotted as a function of time. In a second step the obtained time curve may be noise filtered, for example by averaging across time with sliding window averaging in which a sliding window is applied to a number of consecutive elements and is moved along the entire function. In a third step, the curve is normalized to the first data point or the average of the first n data points, for example 10 points. In a fourth and especially important step, the temporal derivative of this normalized curve is calculated, for example by subtracting neighboring data points and dividing by the temporal resolution (step size, time to repeat 'TR' of the cine pulse sequence) of the temporal series. Such normalized temporal derivative is needed for comparison with said predefined threshold and is hereafter referred to as motion-analog function. A threshold value of 0.002 was empirically found for the heart and is valid in conjunction with the normalized velocity function described below. Other organs or vessels may have different thresholds.

Said first step creates a projection pixel intensity curve as a function of time. In such visualization, blood appears bright in projection pixels acquired with the pre-scan. Therefore the signal level of a projection pixel that goes through the blood cavity is brighter than of a pixel that goes through other tissue. The more bright pixels are collapsed into one projection-pixel the brighter is the projection-pixel. Since cardiac contraction affects the cavity size and with it the number of bright blood pixels combined into one projection-pixel, the brightness of a projection-pixel is a function of the cavity size and varies with the periodic cardiac contraction. Of all projection-pixel versus time curves, those with the largest deviation from a mean signal are most likely to go through the cavity. The curves with the n largest deviations are averaged to create one signal representing cardiac contraction versus time (n=10 preferred). This signal is filtered for noise reduction and normalized to become independent of patient-specific signal-to-noise, coil sensitivity, etc. The temporal derivative of this signal is then calculated to express signal change. It represents a normalized velocity of cardiac contraction or motion of another organ, and small values of the derivative indicate no or minimal motion. It can be regarded as motion-analog function. In one embodiment, this derivative is filtered by sliding window averaging across k points (k=6 preferred), which may be needed if the signal to noise (SNR) of the acquired projection data is low. This optional filtering is in addition to the filtering done in the second step and normalizing done in the third step.

In some embodiments, a threshold region symmetric around zero is defined (between $-\Delta/2$ and $+\Delta/2$) and the time points for which the derivative is within the threshold region are tagged (i.e., labeled) as "no-motion" points in a "no-motion" vector (as referred to herein as a "tag-vector"). The no-motion vector comprises same number of elements as a motion-analog function. The vector may be processed in multiple steps, including knowledge about the minimum duration of the motionless period. Note that this knowledge holds for both normal and diseased hearts. The resulting vector has one or two zones tagged as motionless. One zone usually corresponds to the systolic phase of isovolumetric relaxation, the other to the diastasis phase during diastole. Start and end times of each no-motion region may be detected and provided to the use-sequence. In one embodiment, a sliding median filter is applied to a number of m elements of the no-motion vector and moved along the entire no-motion vector creating a median-filtered no-motion vector. A value of m to cover a time of 25 ms is preferred to remove any small and wrongly tagged regions as consequence of noise remaining in the motion-analog signal despite filtering. This median-filtered no-motion vector may be further filtered replacing its no-motion tagged regions that are shorter than a minimum duration by motion tagged regions. The minimum duration is known from studying hundreds of cardiac cine movies of a random patient population and determining the duration of the one or more motionless periods during the cardiac cycle. In patients with an RR-interval of 600 ms or longer, typically two periods without motion exist: a short systolic period of at least 95 ms duration, and a longer diastolic period much larger than 95 ms. In high-heart rate patients with RR≤600 ms there's typically no diastolic period without motion, and the systolic period of no-motion is shorter than at lower heart rates. Therefore a shorter minimum duration of 65 ms may be used. Consequently the minimum duration of a no-motion tagged region may be based, for example, on the duration of the triggering cycle.

FIGS. 2-27 and the related description below provide details of specific embodiments of the motion assessment technique. Specific values for variables used in the motion assessment technique are used for exemplary purposes. It shall be understood however, that other values may work and that the scope of the motion assessment technique is not limited to the exemplary values.

Figure 2:
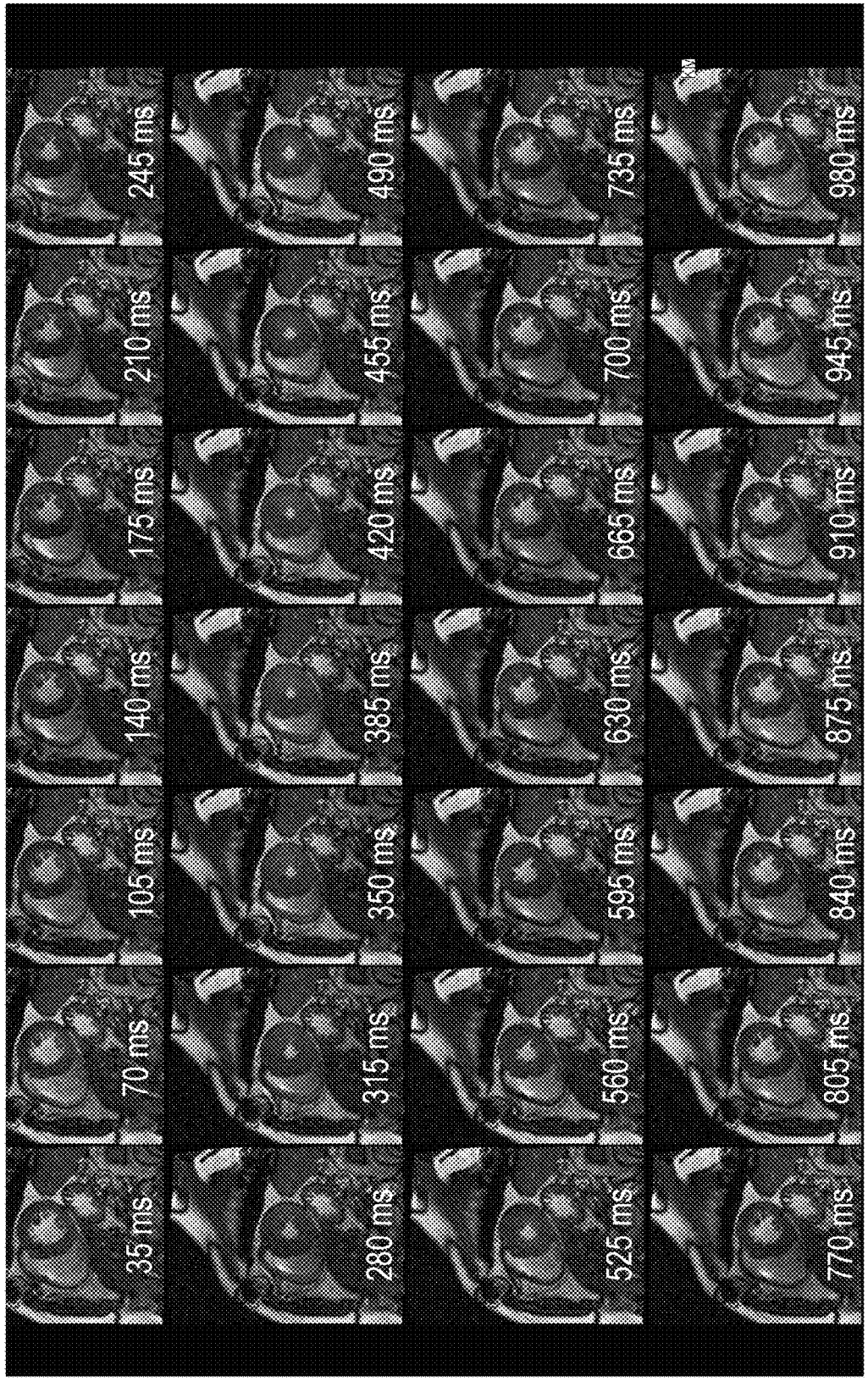
FIG. 2 shows a series of cine frames or cardiac phases of a typical cine MRI acquisition.

FIG. 2 shows a series of cine frames or cardiac phases of a typical cine MRI acquisition. In this example, a short axis view is depicted. The temporal resolution is 35 ms and all 28 cardiac phases are shown filling an RR of about 980 ms. Note that the heart continuously changes its shape and cavity size, but that this patient has two time windows with little or no cardiac motion. Time window 1 occurs between 350 ms and 455 ms and can be used for systolic imaging. Time window 2 is located between 700 ms and 945 ms and shows the period of diastasis, which can be used for diastolic imaging. In this patient, and in most patients with a low or moderate heart rate (RR-interval>800 ms), the second window is longer than the first and is therefore preferred for imaging.

Figure 3:
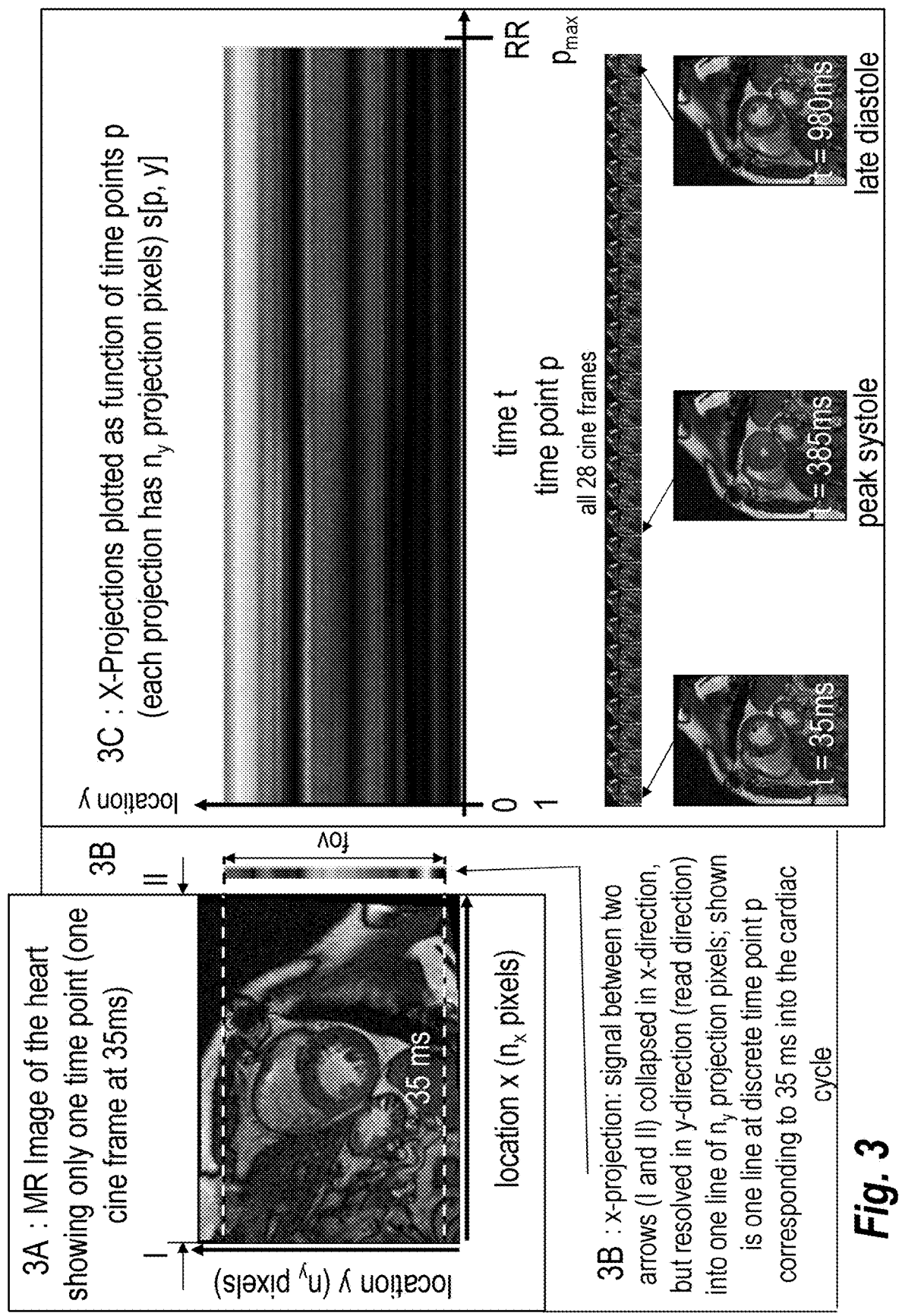
FIG. 3 explains how to obtain a projection image instead of a fully spatially resolved image, according to some embodiments.

FIG. 3 explains how to obtain a projection image instead of a fully spatially resolved image, according to some embodiments. This example shows the first cardiac phase of the cine series of FIG. 2. A projection is created by summing up all pixels of panel 3A along the horizontal direction into a vertical line of single pixels shown in panel 3B. The spatial resolution is lost in (horizontal) x-direction, but preserved in (vertical) y-direction. Note that the pre-scan of the motion assessment technique acquires the line of projection-pixels in the first place. It does not obtain a series of spatially fully resolved cine images first and, it does not then collapse them into a projection series. The fully spatially resolved image in panel 3A is only shown for illustration purposes. The sequence employed by the motion assessment technique never spatially resolves data in the x-direction. The sequence has a field of view (fov) in the y-direction fixed to 256 mm, which is significantly larger than a human heart. It is centered to the same point as the image acquired by the following use-sequence. The preferred number of projection pixels $n_y$ is 128 yielding 2 mm pixel size in y-direction. Slice thickness is set to 10 mm. The acquisition of one line takes the "time-to-repeat" (TR), about 3.5 ms. The same line is acquired repeatedly for about one cardiac cycle (one RR-interval). The preferred implementation acquires for 90% to 95% of the RR so that the next R-wave is not missed for triggering of the use-sequence. For the exemplary RR of 980 ms, the line is acquired at approximately $p_{max}$=95%*980 ms/3.5 ms=266 time points. Panel 3C shows the projection pixel line plotted versus these time points. Slight intensity variations may be appreciated in the center region of the line at about the middle of the RR-interval. The changes can be measured but are small and may not be clearly seen by the human eye. For illustration of these projections' relationship to the cardiac phases, the 28 cine frames from FIG. 2 are plotted in the lower section of panel 2C. Cardiac phases within a no-motion window are zoomed up on. Cine images and projection lines were acquired in the same patient immediately one after the other.

Figure 4:
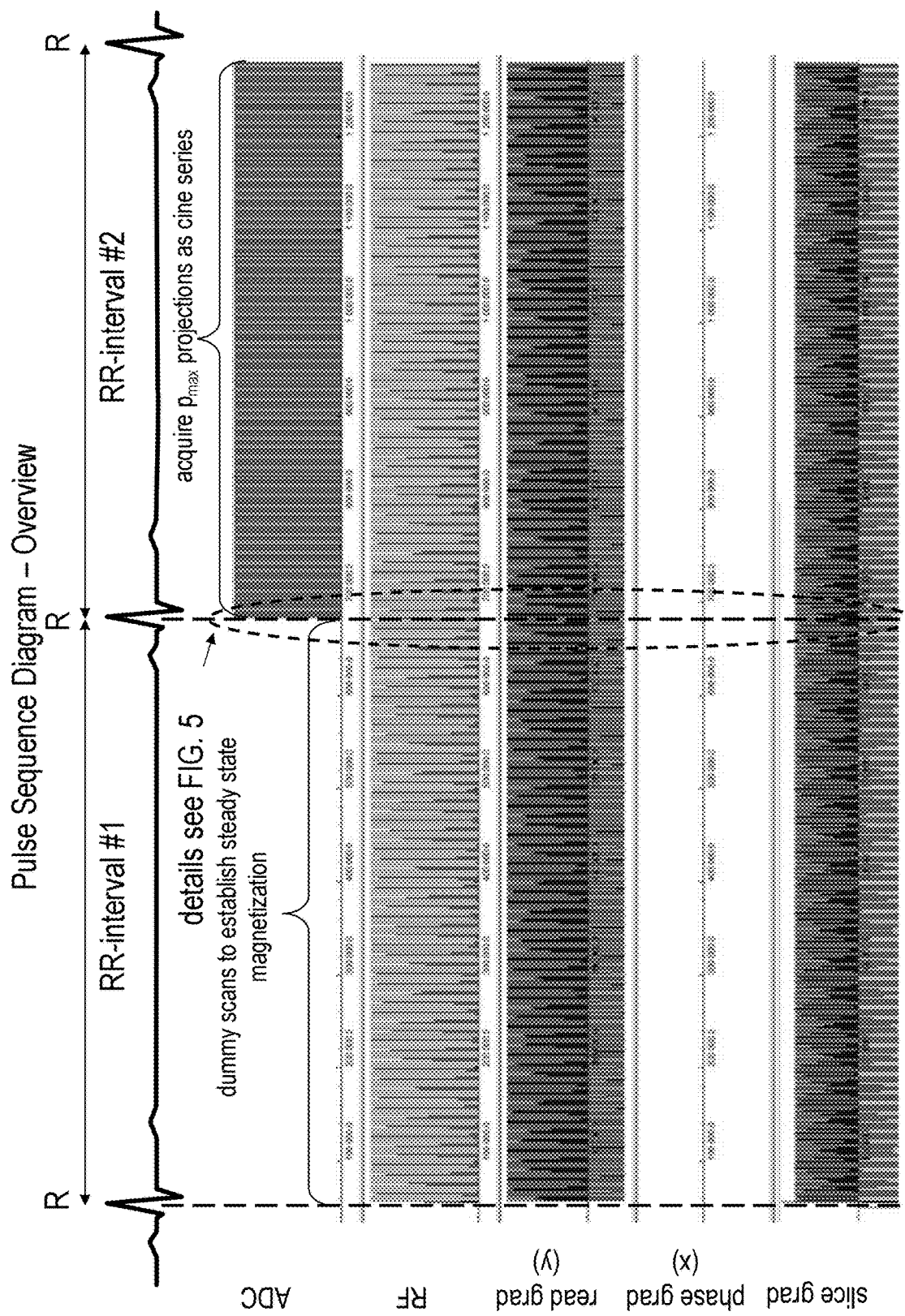
FIG. 4 shows one exemplary implementation of the pre-scan sequence.

FIG. 4 shows one exemplary implementation of the pre-scan sequence. The axes are "analog digital conversion" (ADC) indicating data acquisition, radio frequency (RF) indicating the application of an excitation pulse, "read grad y" for spatial encoding of the y-location, "phase grad x" for spatial encoding of the x-location, and "slice grad" for selecting the imaged slice. Note that no gradients are executed on the "phase grad x" axis, because this projection sequence does not spatially resolve in x-direction. Depicted is a balanced steady state free precession (bSSFP) sequence that is prospectively gated and acquires the same projection line every TR. Two RR-intervals are required by this sequence. During the first RR-interval steady state is established; during the second, the projection lines shown in FIG. 3 are acquired. Note that the acquisition finishes before the last R-wave so that the use-sequence can be triggered with the last R-wave. In case the time between the end of the acquisition and the last R-wave is too short for calculating the time window for the use-sequence, one additional RR is required by the motion assessment technique. The exemplary sequence is a prospectively triggered cine sequence, but the motion assessment technique also works with a retrospectively gated cine scheme. The latter would require part of one additional RR interval. The data processing would be done in the remainder of this RR-interval.

Figure 5:
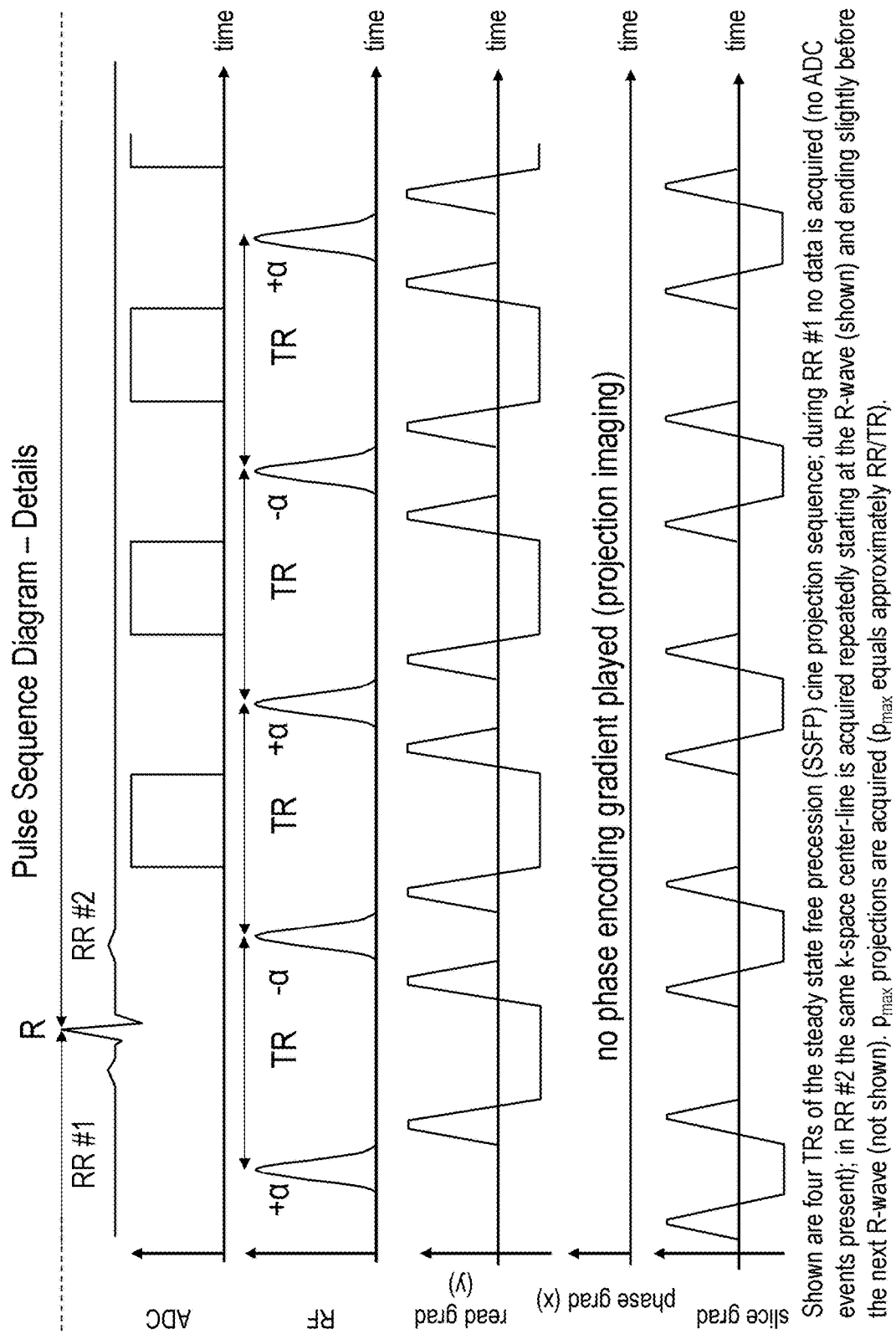
FIG. 5 shows a detailed view of the pre-scan sequence used in the acquisition part of the motion assessment technique.

FIG. 5 shows a detailed view of 4 out of over 250 TR periods of the pre-scan sequence, the acquisition part of the motion assessment technique. The flip angle α is preferably low. For reduction to practice α=15 degrees were used.

Whereas higher values may work, blood inflow into the imaged slice would bring the signal present for higher flip angles out of steady state. As a result, signal variations would no longer be a function of cavity size (and this cardiac contraction) alone, but would be superimposed by flow effects. These effects are advantageously reduced by lowering the flip angle. However, in some embodiments these flow effects may also be emphasized by using a high flip angle on the order of 90 degrees so that periods with maximal or minimal flow can be detected for setting optimal timing of vascular imaging. The sequence is identical to a standard SSFP sequence except that no phase encoding gradient is played since projection data is acquired. The preferred projection direction is head-foot or right-left. Only one of these two options is available in a scanner's slice orientation framework. This depends on the exact slice orientation and in-plane rotation prescribed. Anterior-posterior projections should be avoided, as the bright chest fat can reduce the sensitivity of motion-assessment based on bright blood in the cavity. In some embodiments, a spoiled gradient echo (GRE) sequence is used instead of a SSFP sequence. Utilization of a GRE sequence would not require the leading RR for establishment of steady state and, thus, may save one RR-interval of the total duration of the motion assessment technique. However, GRE images exhibit the typical "lightening effect" at the beginning of the RR-interval (the initial cardiac phases have significantly brighter image intensity than the later ones) and, as a result, a GRE sequence may not be practical as pre-scan.

Figure 6:
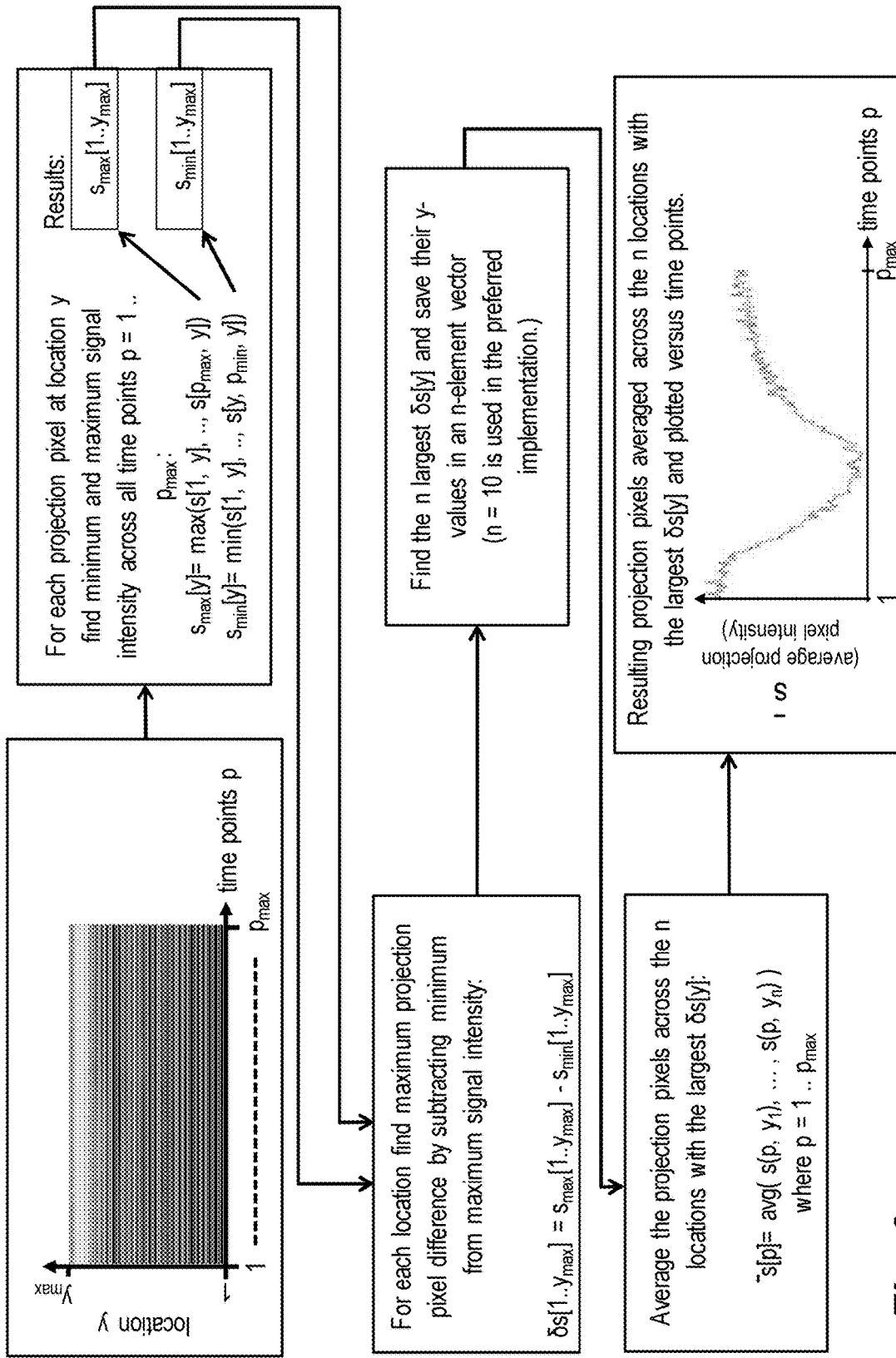
FIG. 6 explains how projection pixels are selected to create a signal analogous to cardiac-contraction.

FIGS. 6-13 review the data processing part of the motion assessment technique. FIG. 6 explains how projection pixels are selected to create a signal analogous to cardiac-contraction. Each projection-pixel is a function of time and is available at $p_{max}$ discrete time points p. In each projection-pixel the minimum and the maximum signal intensities are calculated across these time points. The difference of maximum and minimum is calculated for each projection-pixel as vector δs. Larger signal differences indicate larger changes within the cardiac cycle and are thus more likely projections that go through a (bright) blood region such as the cavity. These projections are preferred as cardiac contraction analog or surrogate signal. To capture a representative sample of cardiac contraction signals and to improve signal-to-noise (SNR) of the measured data the n projections with the largest δs are averaged. The reduction to practice used n=10. The average projection pixel intensity as function of time can be seen on the last (lower right) panel of FIG. 6.

Figures 7A, 7B:
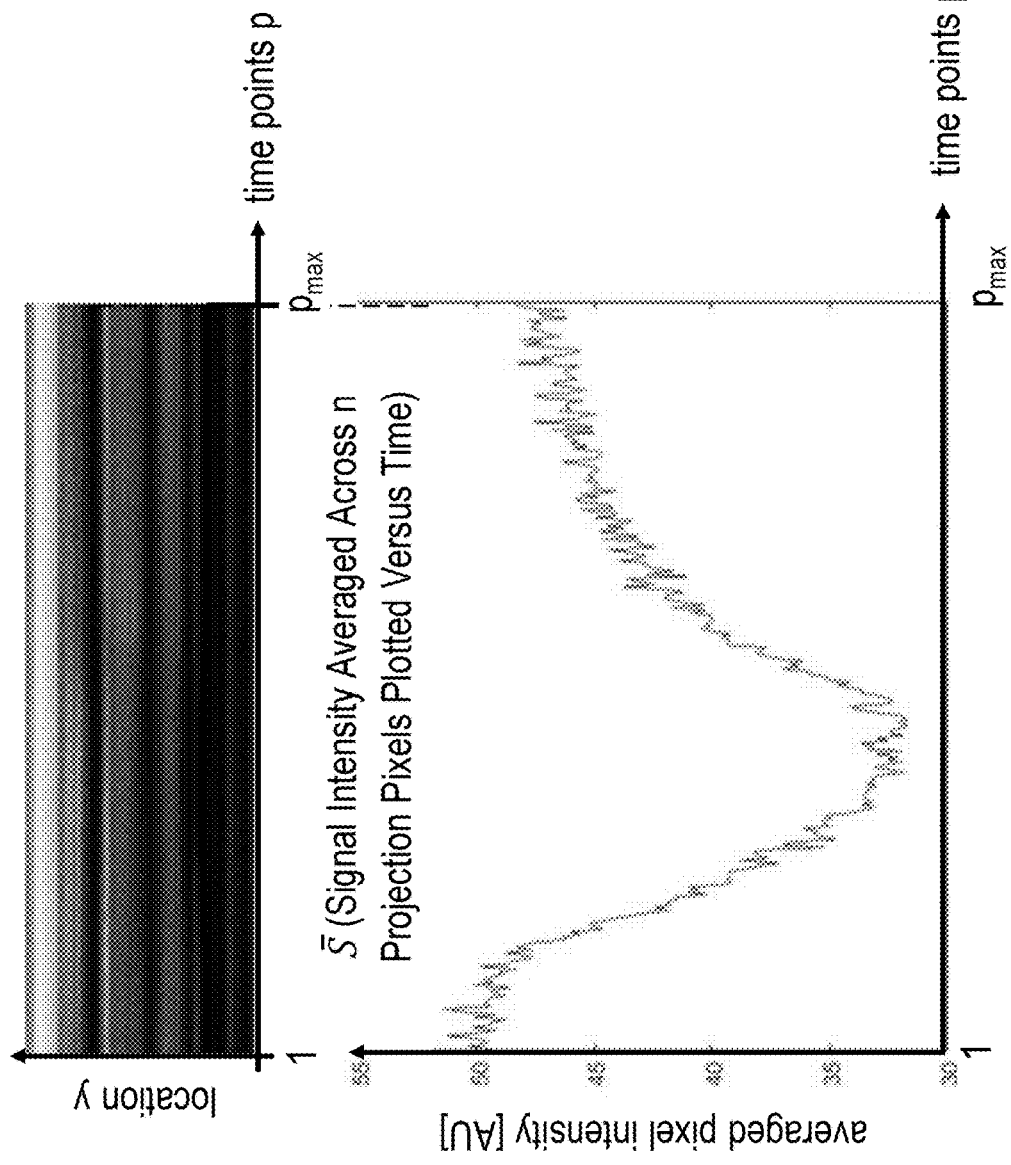
FIG. 7A depicts a magnification of the first (upper left) and the last panel of FIG. 6, showing all projection pixels versus time points.
FIG. 7B shows average pixel intensity of the n projection pixels with the largest difference across time points plotted versus time points for the data shown in FIG. 7A.

FIGS. 7A and 7B show a magnification of the first (upper left) and the last panel of FIG. 6. More specifically, FIG. 7A shows all projection pixels versus time points, and FIG. 7B shows average pixel intensity of the n projection pixels with the largest difference across time points plotted versus time points.

FIGS. 8A and 8B describes the further processing of the cardiac contraction-analog curve of FIG. 7B. FIG. 8A is the result of temporal filtering of the curve from FIG. 7B by a sliding window average filter. k=6 values were averaged during the reduction to practice. The abscissae are interchangeably time axis in milliseconds (ms) or unit less time points axis. The actual data is discrete and saved in vectors or matrices where discrete indices corresponding to the discrete time points are used.

To create signal levels that are independent of a specific patient's SNR, the coils used, the field strength, and the scanner manufacturer, the curve of FIG. 8A is normalized to its averaged first $k_m$ values after the R-wave ($k_m$=10 preferred). It can be assumed without limitation that the cavity has its maximum size after the R-wave. Therefore the signal is close to the maximum and is normalized to 1. The normalized curve is seen in FIG. 8B. Normalizing is important, because the following step depends on fixed number thresholds that only work on normalized data.

FIG. 9A shows the derivative of the normalized curve of FIG. 8B. This derivative represents a motion-analog function. In addition to calculating the derivative, the curve was also filtered by sliding window averaging (again using k=6 values preferred). This may or may not be needed, depending on the SNR of the acquired data. A derivative depicts change over time, or motion. A derivative of zero means "no-motion". A small value of the derivative means minimal motion. In this example, a region from −Δ/2 to +Δ/2 is defined as the "no-motion" region. We empirically found a value of Δ=0.004 to work well in a broad selection of patients with normal and diseased hearts, high, normal, and low heart rates, of all ages and genders.

FIG. 9B shows a vector $V1_{NM}(p)$ which has each time point tagged as possessing cardiac motion or not. If the derivative is within −Δ/2 to +Δ/2 a point is tagged as having "no-motion" and the respective vector element e is set to 1, otherwise to 0. Note that the region between 600 ms and 720 ms has multiple oscillations between 0 and 1. These are either caused by the noise in the signal or true rapid changes in motion.

Figure 10:
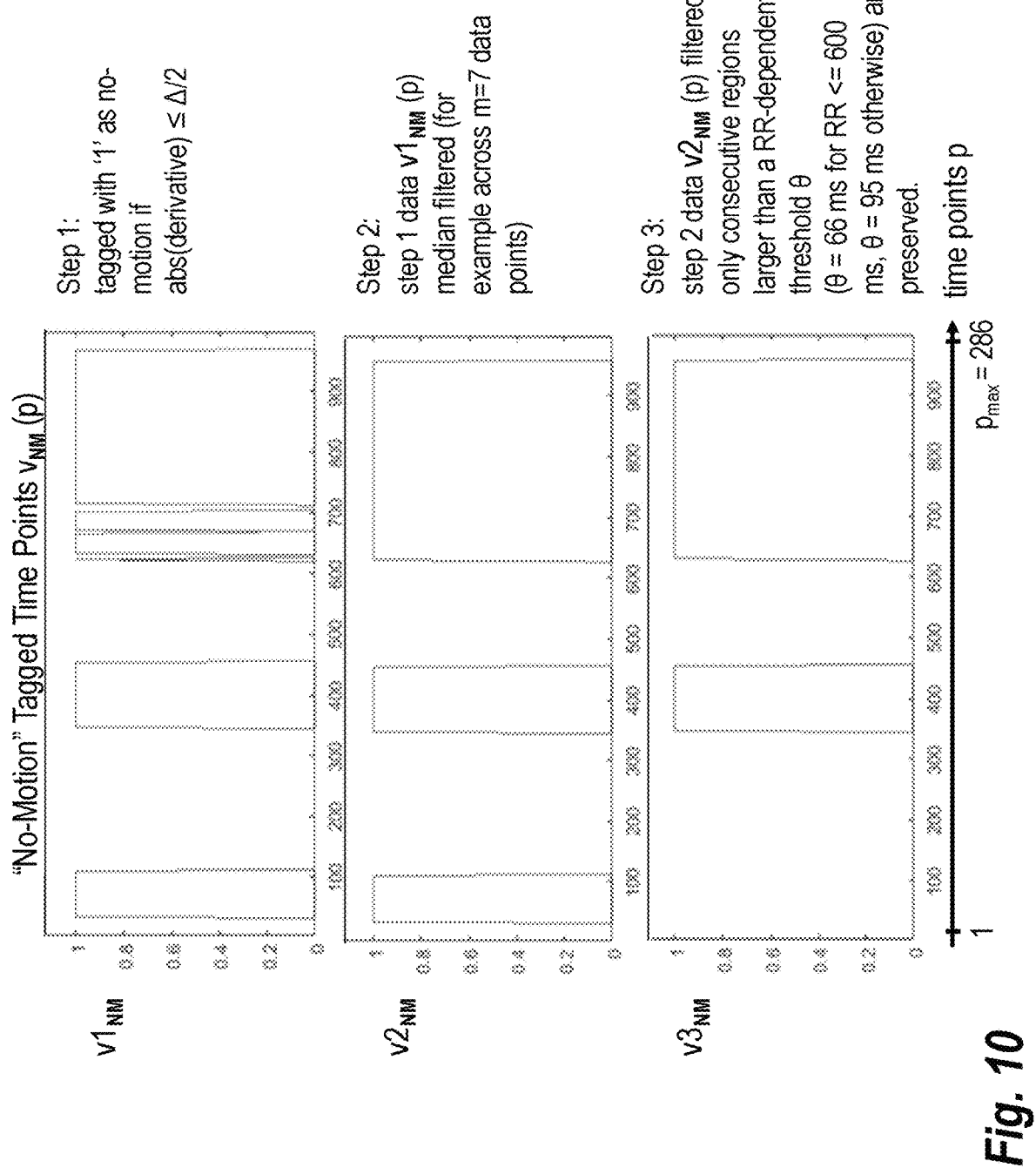
FIG. 10 shows the no-motion tagged vector on top, the results of its median filtering in the middle, and the results of further processing according to temporal threshold $\theta$ on the bottom, with two calculated "no-motion" regions with respective start and end times.
Figure 11:
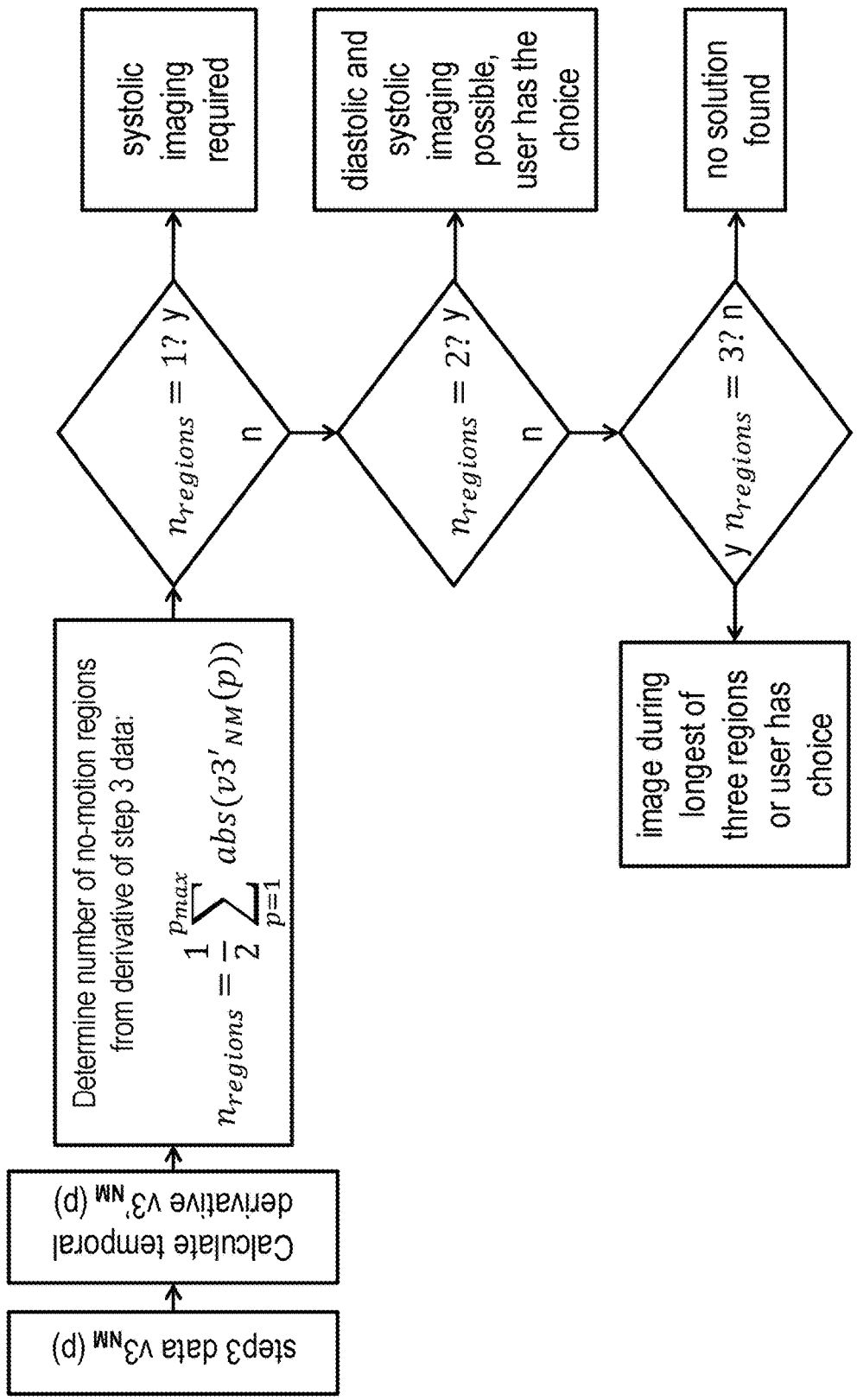
FIG. 11 shows the flow chart of an example algorithm for calculating the number of "no-motion" regions $n_{regions}$ and the selection of the "no-motion" window, according to some embodiments of the present invention.

FIG. 10 shows the no-motion tagged vector on top, the results of its median filtering in the middle, and the results of further processing according to temporal threshold θ on the bottom, with two calculated "no-motion" regions with respective start and end times. The top plot in FIG. 10 is identical to FIG. 9B. Because it is the goal of the motion assessment technique to create continuous "no-motion" regions, the above described oscillatory regions are not wanted. They are removed by a median filter applied to $V1_{NM}(p)$ resulting in $V2_{NM}(p)$ shown in the middle plot FIG. 10. The preferred implementation filters across m=7 points. The bottom plot in FIG. 10 shows the result of the third filtering step, $V3_{NM}(p)$. This filter removes any no-motion region that is shorter than a known threshold θ. We empirically found a value of θ=66 ms to work well for RR≤600 ms and θ=95 ms in the same varied patient population from above. The filter removes the "no-motion" region right after the R-wave as it is always shorter than the periods for systolic and diastolic imaging. By making the value θ shorter one can include shorter no-motion periods into the no-motion vector, for example, imaging right at the R-wave FIG. 11 shows the flow chart of an example algorithm for calculating the number of "no-motion" regions $n_{regions}$ and the selection of the "no-motion" window, according to some embodiments of the present invention. The first step creates the discrete temporal derivative $v3'_{NM}(p)$ by subtracting data of two consecutive time points: $v3'_{NM}(p)=v3_{NM}(p)-v3_{NM}(p-1)$. The resulting vector has one of three values −1 (transition from "no-motion" to motion region), 0 (remaining in one region), and +1 (transition from motion to "no-motion" region). By summing up the absolute values of this vector the number of transitions is found. The number of regions equals half the transitions. If a single region is found then this always is a systolic region. This is usually the case for high heart rates when the diastasis period is too short to be used for imaging. If two regions are found, one will be diastolic and the other systolic. A known user preference would then decide on which of the windows to use. For hearts that are, for example, severely dilated and therefore hardly change shape during the cardiac cycle, more than two "no-motion" regions may be found. By default, the algorithm picks the longest of them. A known user preference can be queried to change this behavior.

Figure 12:
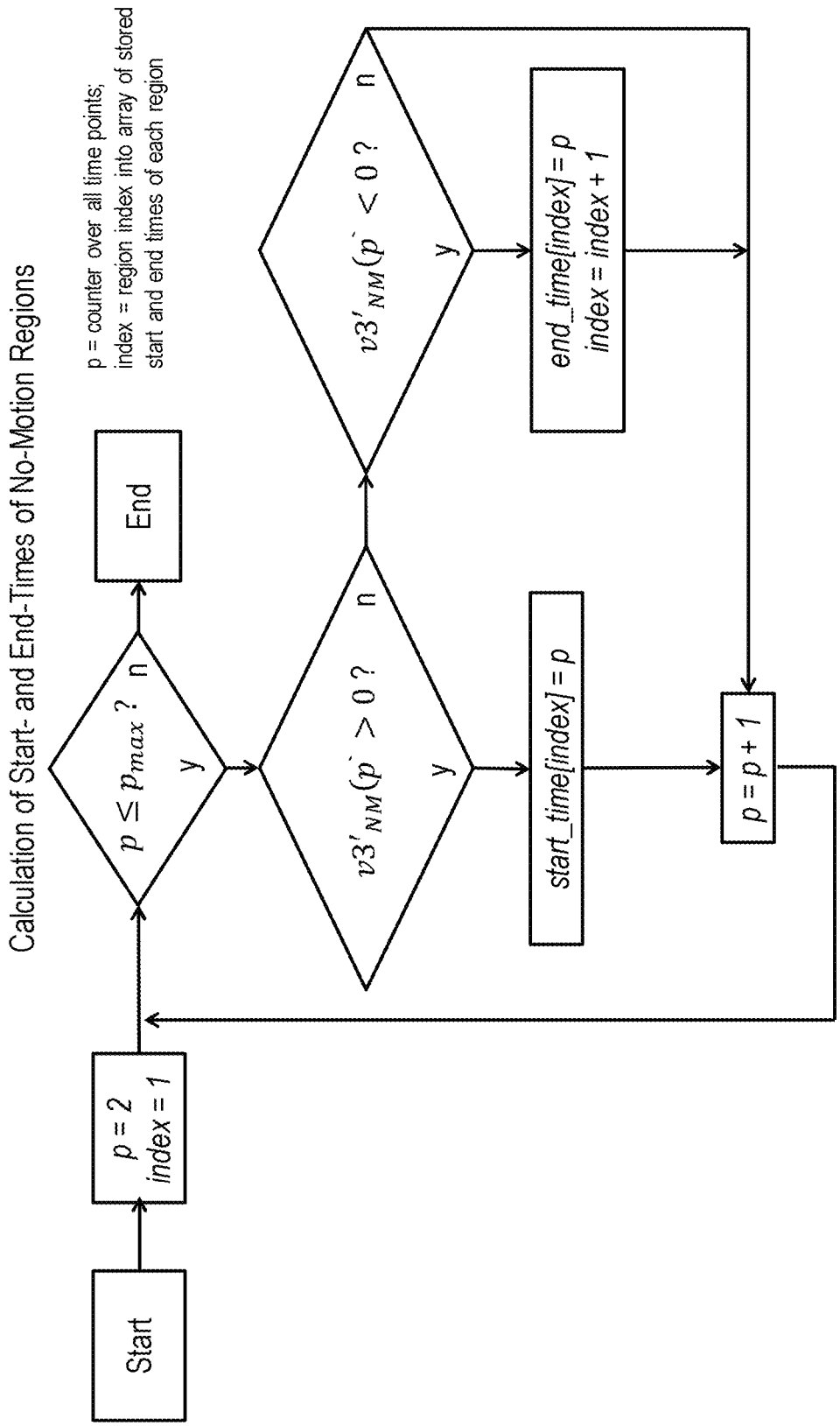
FIG. 12 shows an example flow chart for calculating the start and end times of all no-motion regions found, according to some embodiment.

FIG. 12 shows an example flow chart for calculating the start and end times of all no-motion regions found, according to some embodiment. This example also operates on the temporally derived data and its possible values −1, 0, and +1.

The results obtained by applying the algorithms shown in FIGS. 11 and 12 to the data of FIGS. 7 to 10 were as follows. One systolic and one diastolic region were found. For the systolic region, the results were start time=346.92 ms; end_time=456.66 ms; and duration=113.28 ms. For the diastolic region, the results were start_time=630.12 ms; end_time=959.34 ms; and duration=332.76 ms. Comparison with the cine of the same patient in FIG. 2 proves that the algorithm calculated the "no-motion" regions correctly.

FIGS. 13 to 27 show data of three additional patients. The comparisons of the motion assessment technique-provided "no-motion" region or regions with the accompanying cines show the proper function of the motion assessment technique.

Figure 13:
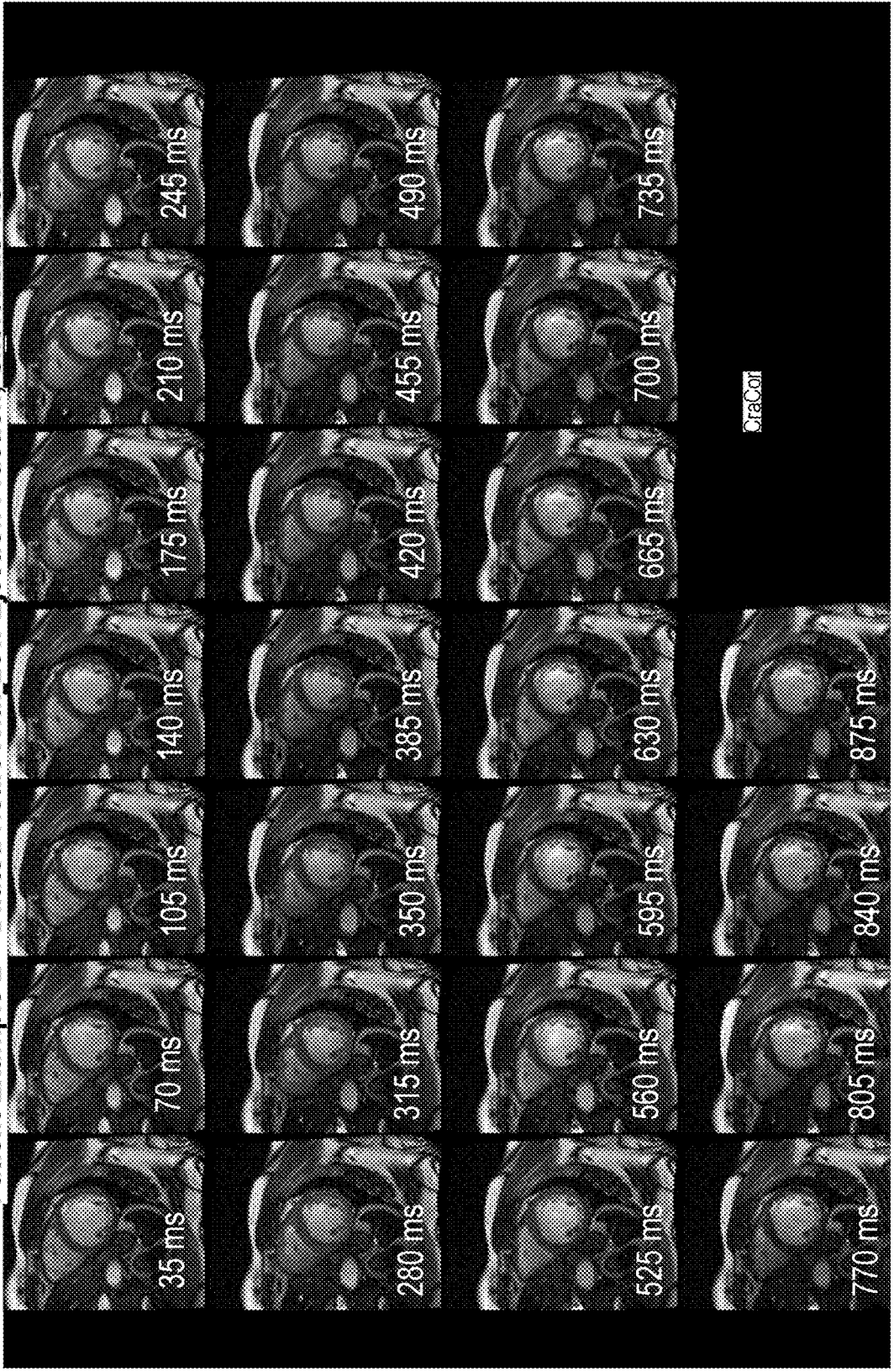
FIG. 13 shows the cine frames of a dilated heart with low ejection fraction and poor contractile function in a short-axis view.
Figure 16A:
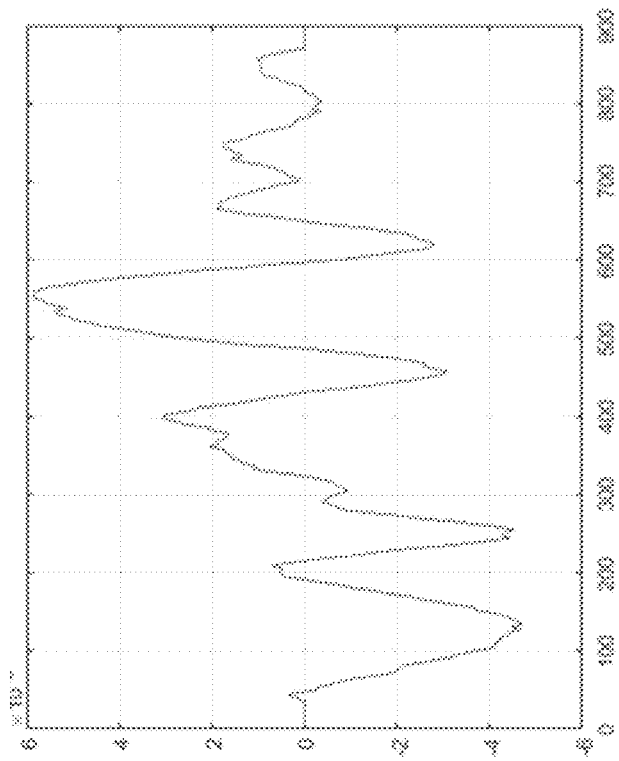
FIG. 16A shows the derivative of the normalized curve of FIG. 15B.
Figure 16B:
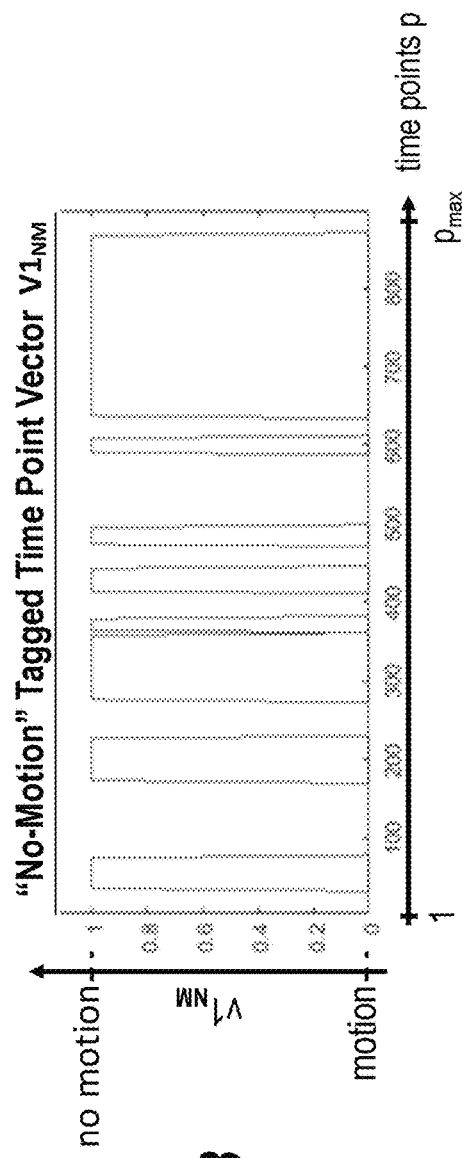
FIG. 16B shows a vector $V1_{NM}(p)$ which has each time point tagged as possessing cardiac motion or not, with respect to the data shown in FIG. 16A.

FIG. 13 shows the cine frames of a dilated heart with low ejection fraction and poor contractile function in a short-axis view.

Figure 17:
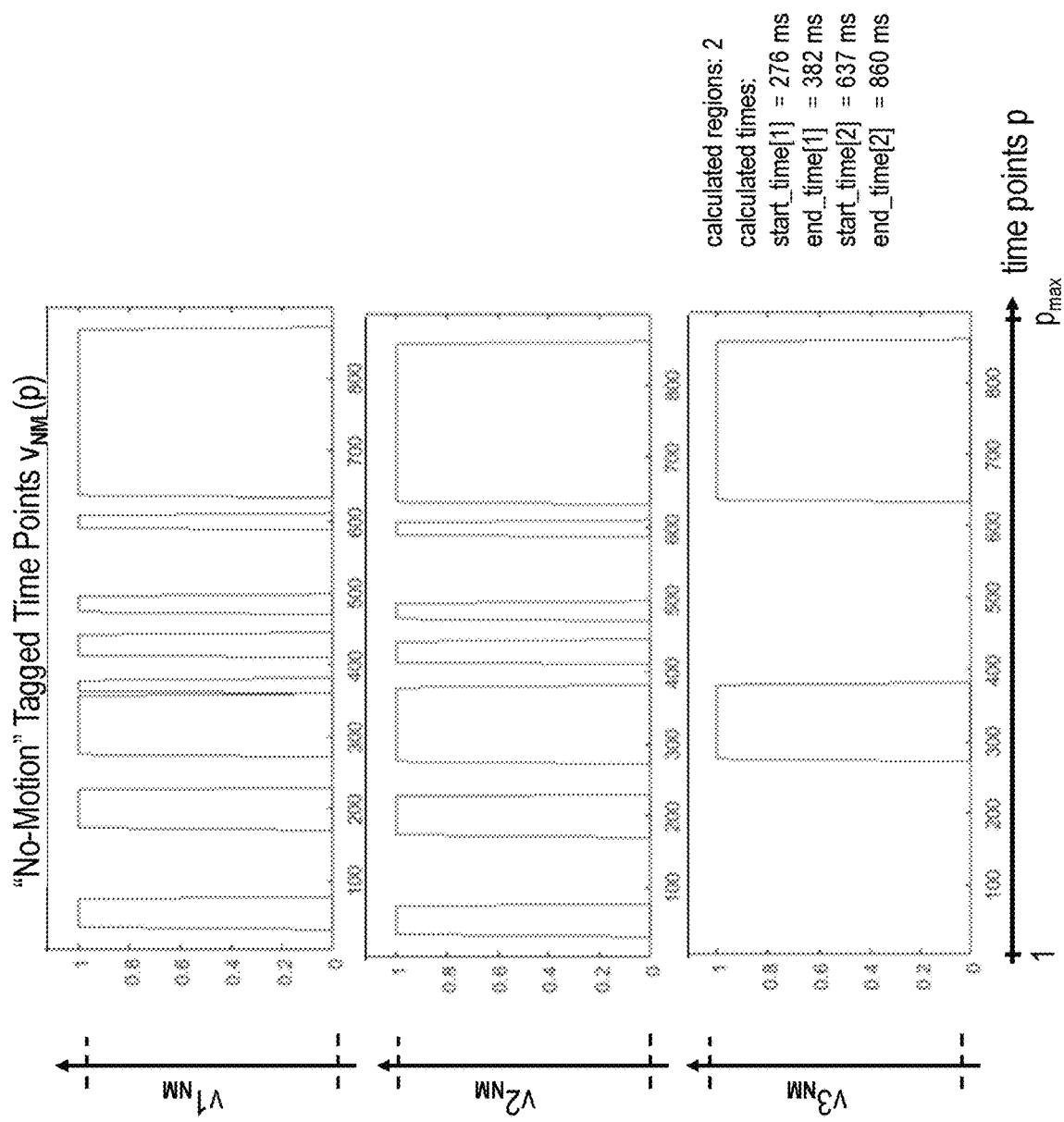
FIG. 17 shows the no-motion tagged vector on top, the results of its median filtering in the middle, and the results of further processing according to temporal threshold $\theta$ on the bottom, with two calculated "no-motion" regions with respective start and end times.

FIGS. 14 to 17 show the data of this patient processed by the same steps as in the previous example, according to motion assessment technique principles. Thus, FIG. 14A shows all projection pixels versus time points. FIG. 14B shows the average pixel intensity of the n projection pixels with the largest difference across time points plotted versus time points. FIG. 15A illustrates smoothing data by sliding time window averaging, while FIG. 15B illustrates the data normalizing step. FIG. 16A shows the derivative of the normalized curve of FIG. 15B. FIG. 16B shows a vector $V1_{NM}(p)$ which has each time point tagged as possessing cardiac motion or not. FIG. 17 shows the no-motion tagged vector on top, the results of its median filtering in the middle, and the results of further processing according to temporal threshold θ on the bottom, two calculated "no-motion" regions with respective start and end times.

Figure 18:
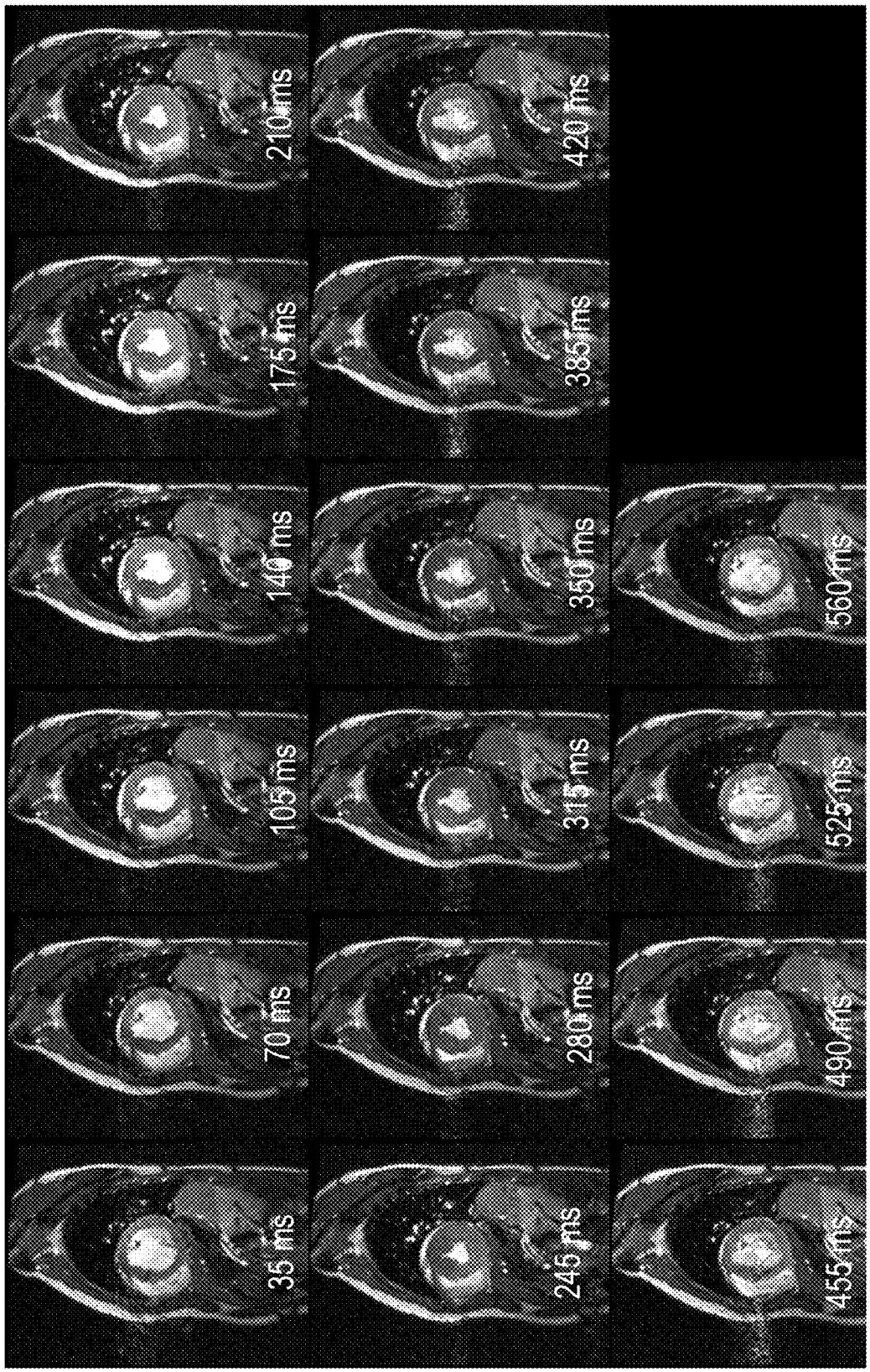
FIG. 18 shows the cine frames of a third patient with high heart rate (about 110 beats per minute) and an extremely short period of diastasis, in a short-axis view.

FIG. 18 shows the cine frames of a third patient with high heart rate (about 110 beats per minute) and an extremely short period of diastasis, in a short-axis view.

Figures 19A, 19B:
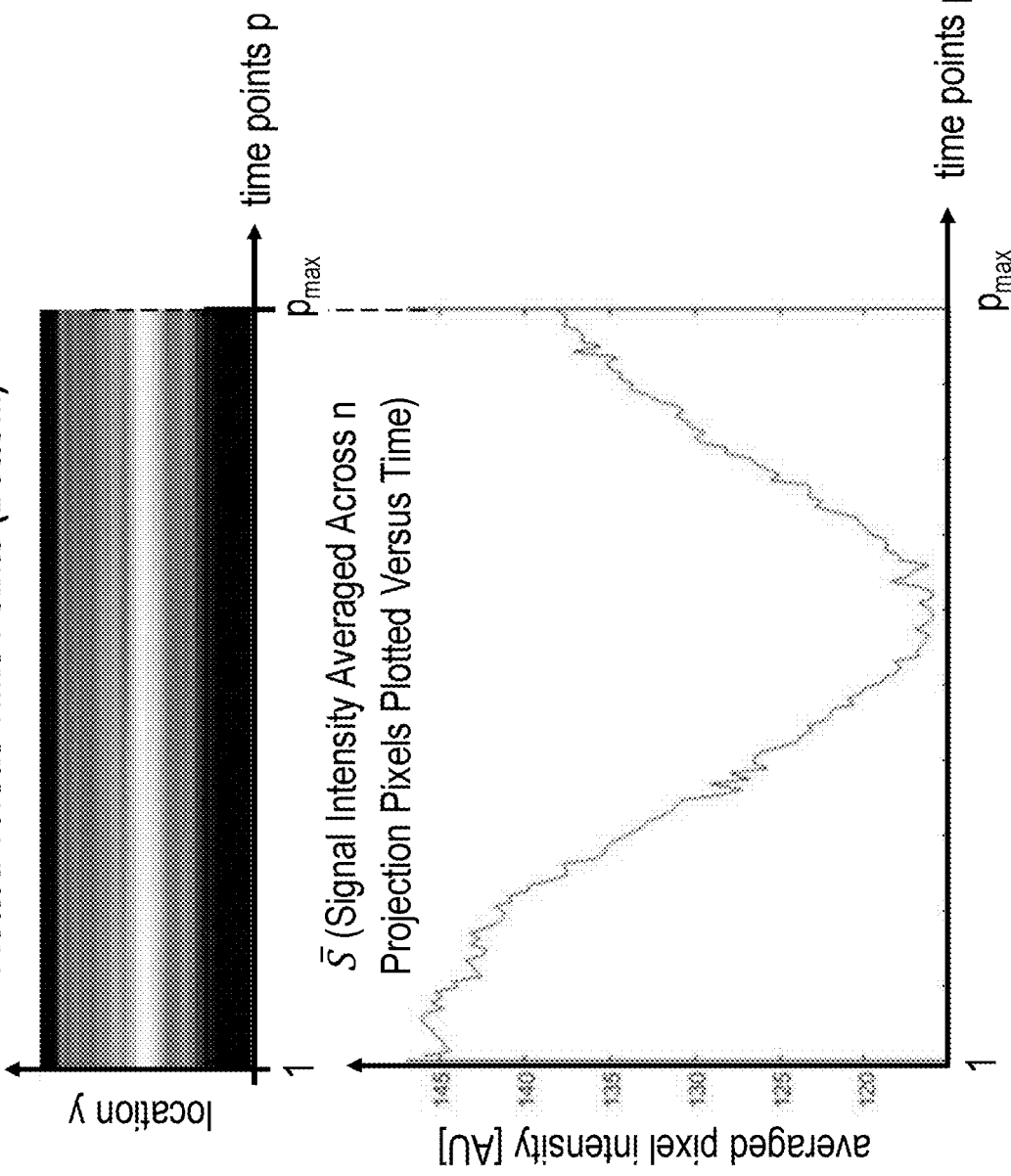
FIG. 19A depicts a magnification of the first (upper left) and the last panel of FIG. 18, showing all projection pixels versus time points for the third patient.
FIG. 19B shows average pixel intensity of the n projection pixels with the largest difference across time points plotted versus time points for the data shown in FIG. 19A.
Figure 21A:
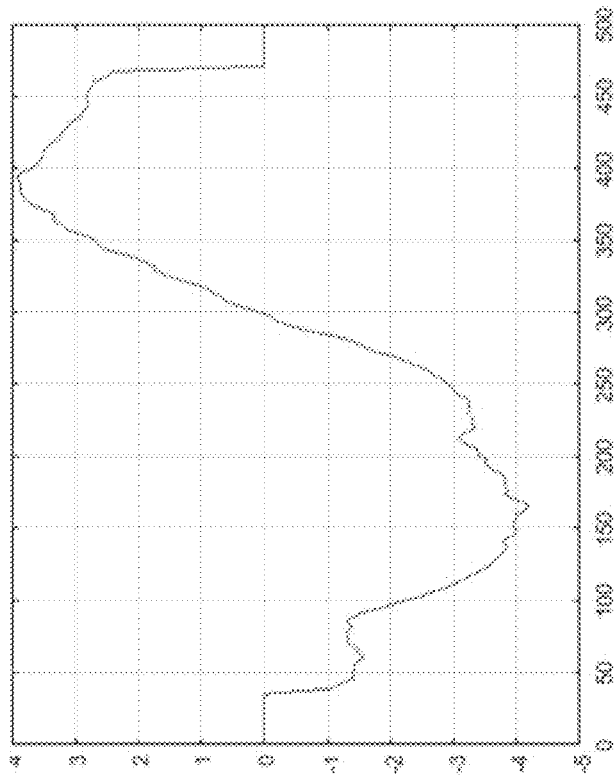
FIG. 21A shows the derivative of the normalized curve of FIG. 20B.
Figure 21B:
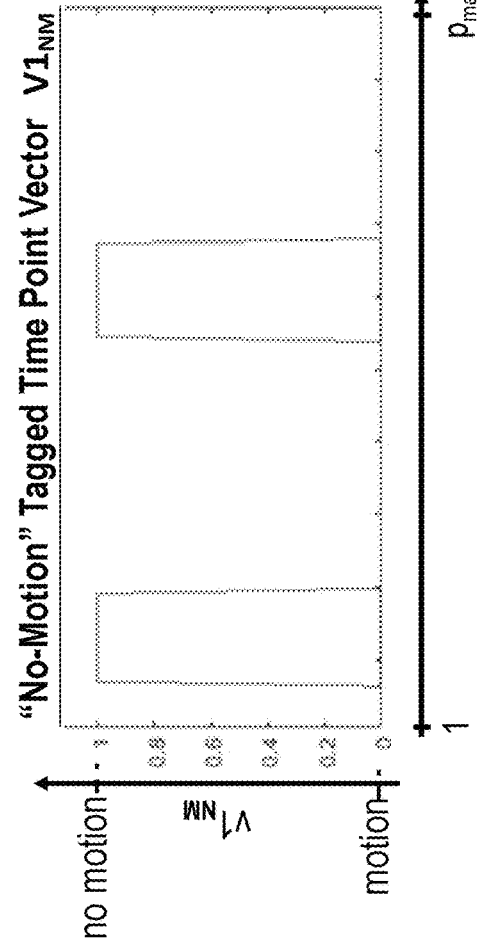
FIG. 21B shows a vector $V1_{NM}(p)$ which has each time point tagged as possessing cardiac motion or not, with respect to the data shown in FIG. 21A.
Figure 22:
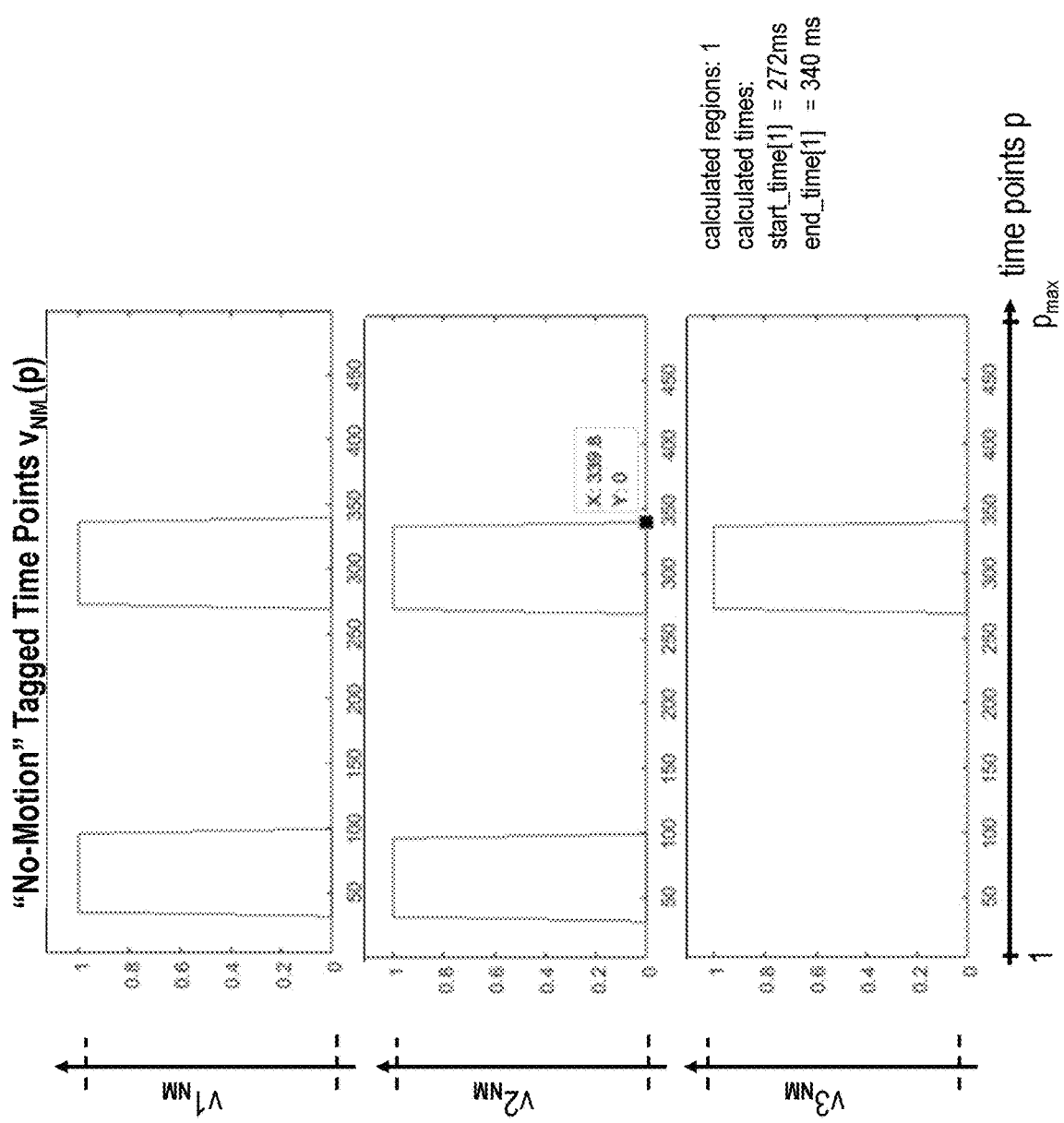
FIG. 22 shows the no-motion tagged vector on top, the results of its median filtering in the middle, and the results of further processing according to temporal threshold $\theta$ on the bottom, with two calculated "no-motion" regions with respective start and end times.

FIGS. 19A to 22 show the data of this patient processed by the same steps as in the previous example, according to motion assessment technique principles. More specifically, FIG. 19A shows all projection pixels versus time points. FIG. 19B shows the average pixel intensity of the n projection pixels with the largest difference across time points plotted versus time points. FIG. 20A shows the data smoothing by sliding time window averaging, and FIG. 20B the normalizing of the smoothed data of FIG. 20A. FIG. 21A shows the derivative of the normalized curve of FIG. 20B. FIG. 21B shows a vector $V1_{NM}(p)$ which has each time point tagged as possessing cardiac motion or not. Finally, FIG. 22 shows the no-motion tagged vector on top, the results of its median filtering in the middle, and the results of further processing according to temporal threshold θ on the bottom, one calculated "no-motion" region with its respective start and end_time. Note that the motion assessment technique correctly identified only a systolic imaging region and no diastolic region, because there was no or only an extremely short motionless period present during diastole.

Figure 23:
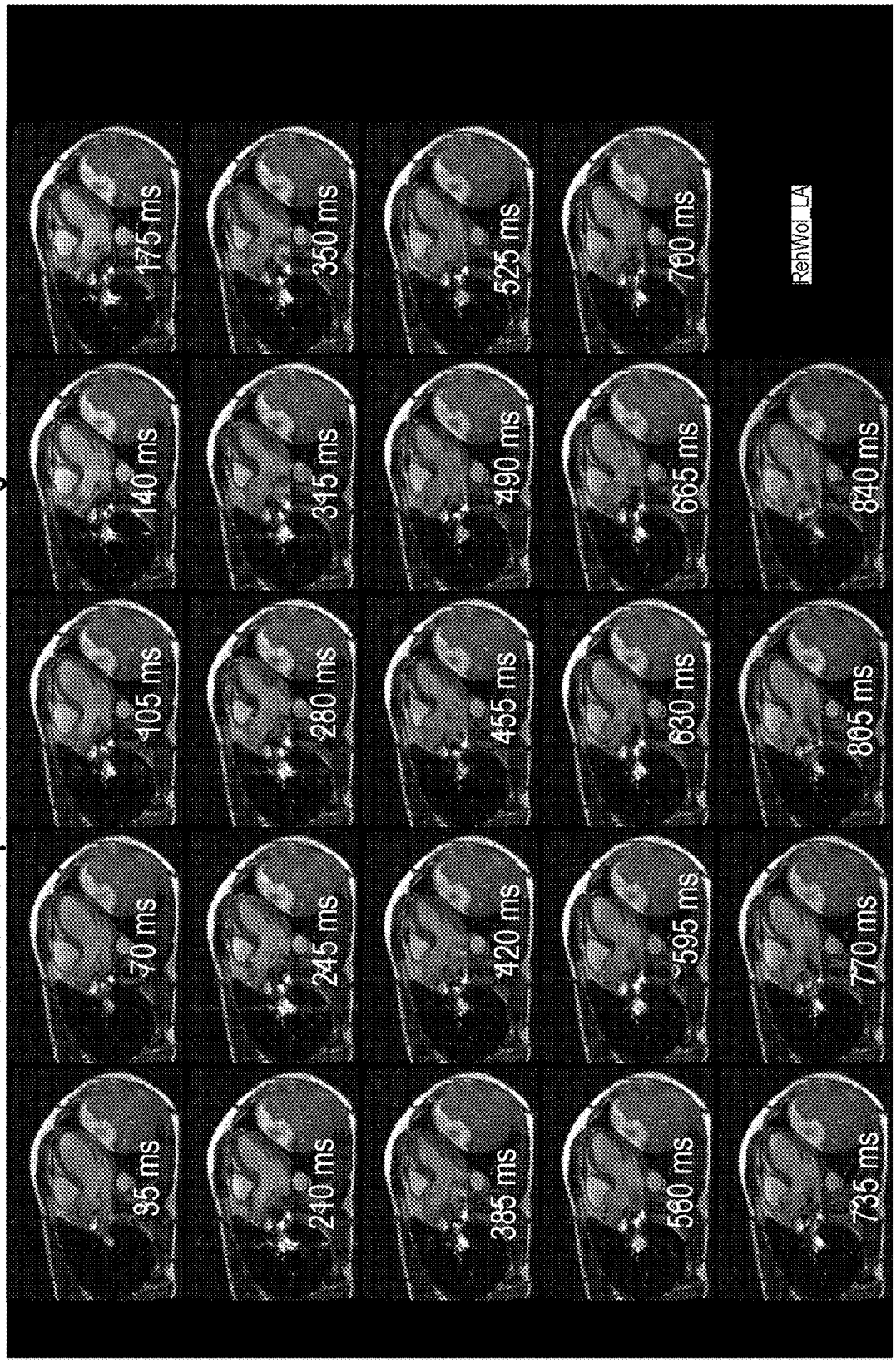
FIG. 23 shows the cine frames of a fourth patient with a normal heart, in a long-axis view.
Figures 24A, 24B:
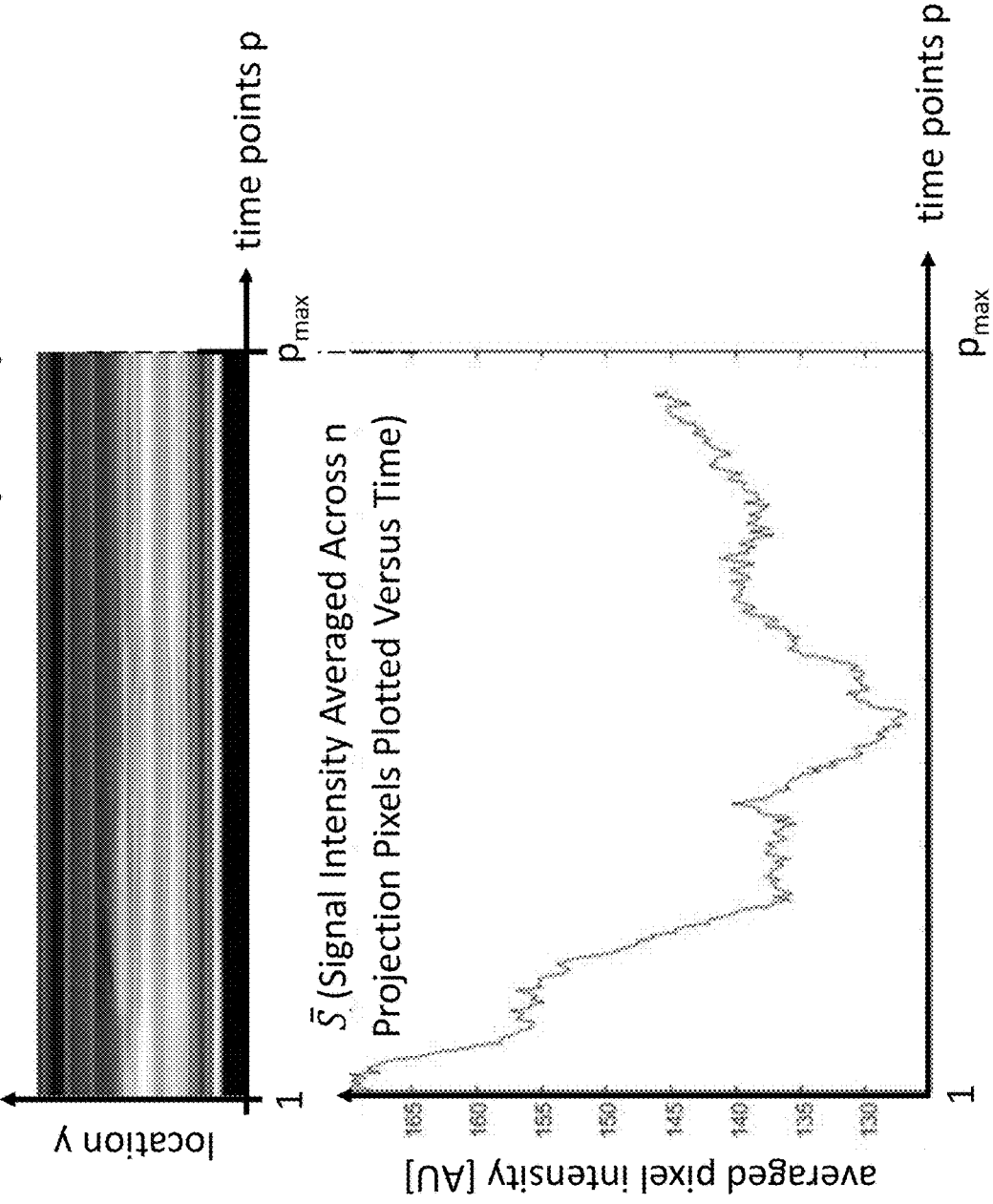
FIG. 24A depicts a magnification of the first (upper left) and the last panel of FIG. 23, showing all projection pixels versus time points for the fourth patient.
FIG. 24B shows average pixel intensity of the n projection pixels with the largest difference across time points plotted versus time points for data shown in FIG. 24A.
Figure 26A:
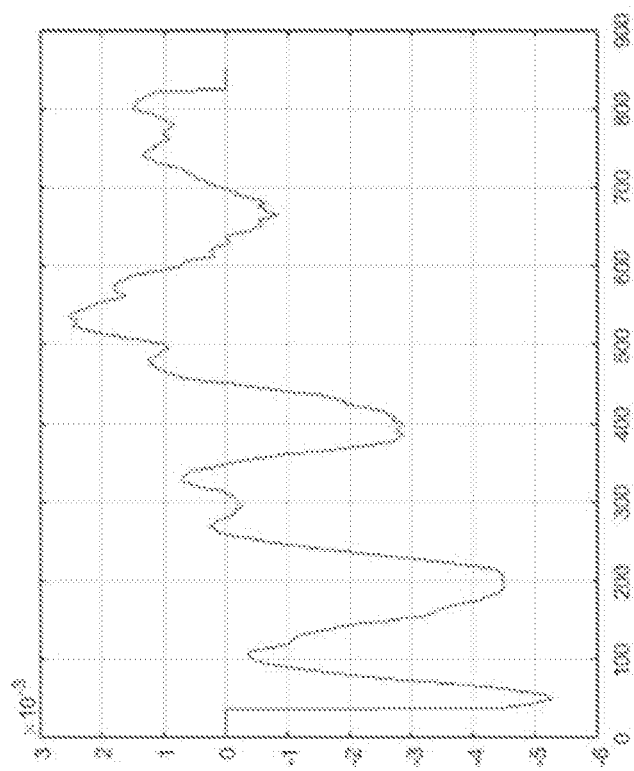
FIG. 26A shows the derivative of the normalized curve of FIG. 25B.
Figure 26B:
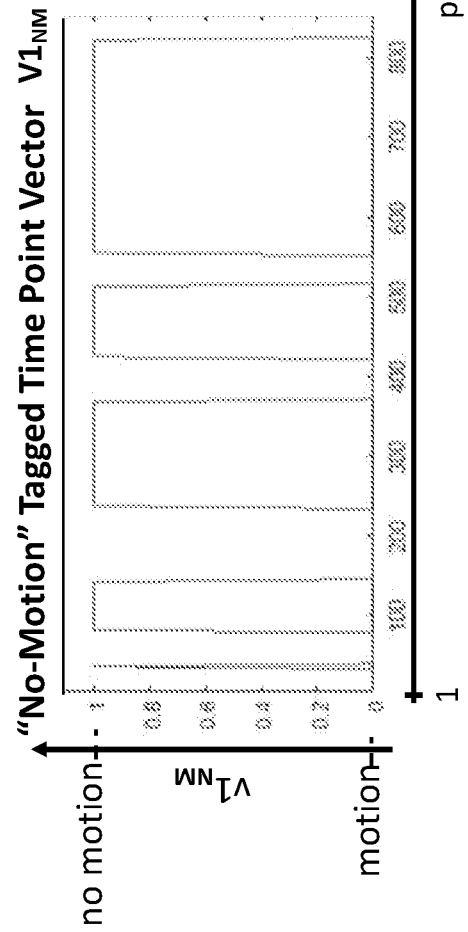
FIG. 26B shows a vector $V1_{NM}(p)$ which has each time point tagged as possessing cardiac motion or not, with respect to the data shown in FIG. 26A.

FIG. 23 shows the cine frames of a fourth patient with a normal heart, in a long-axis view. The purpose of this example is to demonstrate that the motion assessment technique works in different view orientations, not just short axis views.

Figure 27:
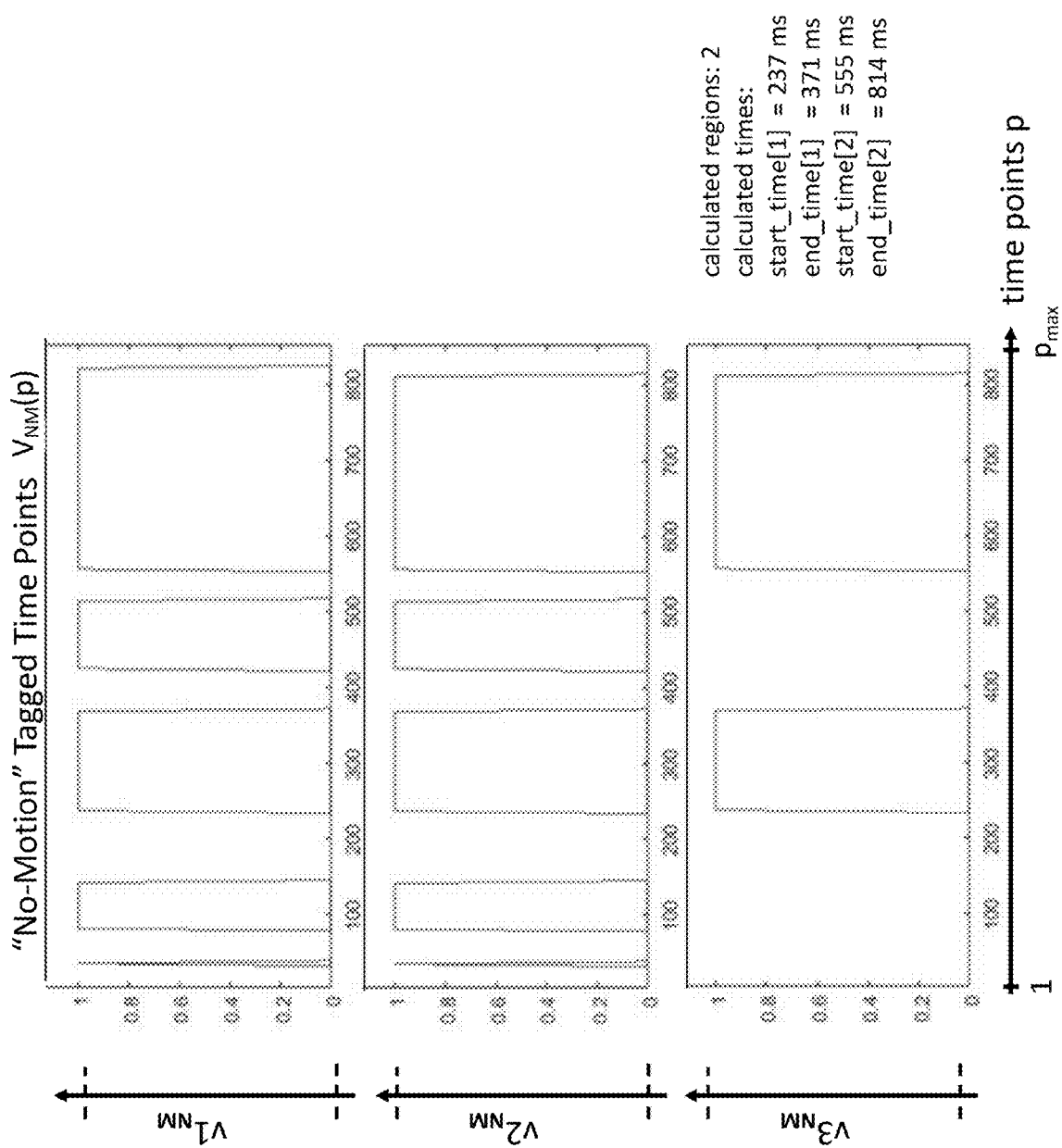
FIG. 27 shows the no-motion tagged vector on top, the results of its median filtering in the middle, and the results of further processing according to temporal threshold $\theta$ on the bottom, with two calculated "no-motion" regions with respective start and end times.

FIGS. 24 to 26B show the data of this patient processed by the same steps as in the previous example, according to motion assessment technique principles. FIG. 27 shows the no-motion tagged vector on top, the results of its median filtering in the middle, and the results of further processing according to temporal threshold θ on the bottom, two calculated "no-motion" regions with their respective start and end times. The heart rate was relatively low and the two motionless regions are therefore relatively long, as is also observable in the cine frames. The motion assessment technique correctly identified these regions regarding start, duration, and end times.

The motion assessment technique described herein provides various benefits over conventional technologies. For example, the disclosed techniques can be used with an ECG as well as with a pulse-oximetry "pulse-ox" trigger system. Conventional vendor provided logic for setting timing parameters to select the motionless period does not work with a pulse-ox trigger, because its trigger signal is delayed relative to the R-wave, but the exact time delay is unknown. The time delay is patient dependent and varies even in a single patient based on the current heart rate, blood pressure, vessel compliance, among other factors. The motion assessment technique overcomes the problem of unknown delay as it assesses motion relative to the provided trigger signal and finds the motionless period relative to the current trigger signal regardless of its source (ECG or pulse-ox). Since the motion assessment technique is executed immediately before the use-sequence, the found timing parameters are current and optimal.

Figure 28:
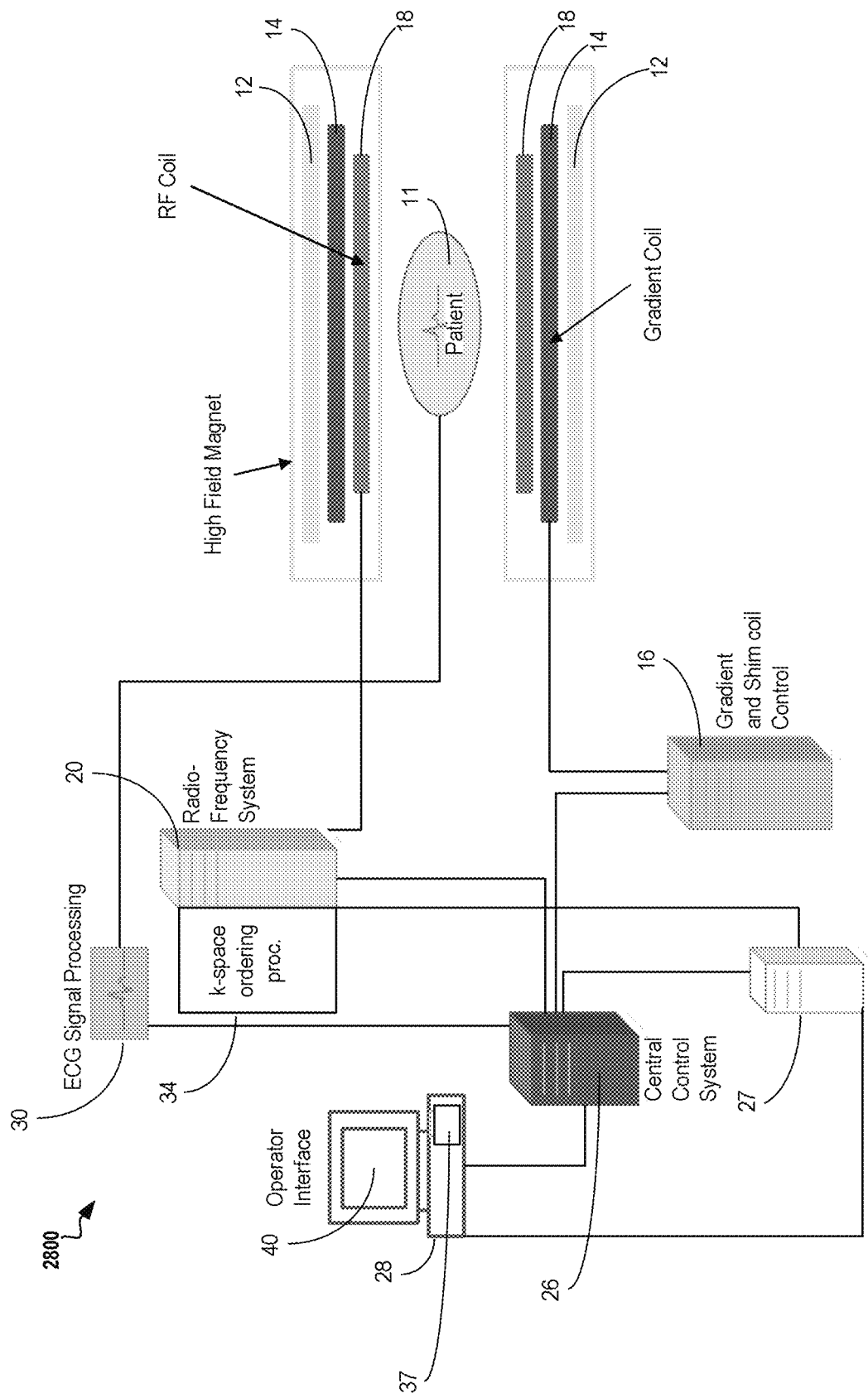
FIG. 28 shows a system for ordering acquisition of frequency domain components representing MR image data for storage in a k-space storage array, as used by some embodiments of the present invention.

Another advantage of the motion assessment technique described herein is that it works for any given healthy or diseased heart, because it analyzes the individual heart's motion and does not rely on properties of a normal heart. For example, a dilated poorly contracting heart may have a motionless period which occurs at a different time window relative to the R-wave and which may be longer than in a healthy heart, even for the same heart rate. Therefore an algorithm based on a healthy heart's RR duration would not reliably set the no-motion window, but the motion assessment technique finds it, because it operates on data measured in the actual patient rather than on a-priori knowledge obtained from a normal heart FIG. 28 shows a system 2800 for ordering acquisition of frequency domain components representing MR image data for storage in a k-space storage array, as used by some embodiments of the present invention. In system 2800, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further RF (radio frequency) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising an MR dataset. The k-space array of individual data elements has a designated center and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components are sequentially acquired during acquisition of an MR dataset representing an MR image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and the magnetic field gradient change between successively acquired frequency components is substantially minimized.

Central control unit 26 uses information stored in an internal database to process the detected MR signals in a coordinated manner to generate high quality images of a selected slice(s) of the body (e.g., using the image data processor) and adjusts other parameters of system 2800. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Display processor 37 processes the magnetic resonance signals to provide image representative data for presentation on display 40, for example.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning a processor to implement predetermined functions, such as those of an operating system, an imaging system (see e.g., FIG. 28) or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U. S. C. 112(f), unless the element is expressly recited using the phrase "means for."

I claim:

1. A method for determining time periods of minimal motion of a physiologic organ relative to a trigger of a physiologic triggering signal and within a triggering cycle, the method comprising:
   monitoring the physiologic triggering signal associated with a patient;
   using an MRI cine pulse sequence to acquire a temporal series of projections across a region of interest comprising an organ of interest; and
   analyzing the temporal series of projections to determine one or more times relative to a trigger provided by the physiologic triggering signal during which motion of the organ of interest is below a predefined threshold, wherein motion of the organ of interest is assessed by a process comprising:
   (a) creating a signal intensity versus time curve of one pixel or an average of multiple pixels included in the temporal series of projections,
   (b) applying a noise filter and normalization to the signal intensity versus time curve to yield a filtered and normalized time curve,
   (c) determining the temporal derivative of the filtered and normalized time curve to yield a motion-analog function,
   (d) evaluating the absolute value of the motion-analog function for being smaller than the predefined threshold to determine the one or more times, and
   (e) tagging elements for which an absolute value of the derivative is below a predefined threshold as having no motion in a tag-vector comprising a same number of elements as a motion-analog function.

2. The method of claim 1, wherein the projections are repeatedly acquired at same locations at consecutive times during at least 90% of one triggering cycle.

3. The method of claim 1, wherein the signal intensity versus time curve is an average of a plurality of pixels in each projection in the series of projections across all time points.

4. The method of claim 1, wherein the motion-analog function is averaged across time with sliding window averaging in which a sliding window is applied to a number of consecutive elements and is moved along entire the motion-analog function.

5. The method of claim 1, wherein a sliding median filter is applied to the tag-vector and moved along the entire tag-vector creating a median-filtered tag-vector.

6. The method of claim 5, wherein the median-filtered tag-vector is further filtered replacing its no-motion tagged regions that are shorter than a minimum duration by motion tagged regions.

7. The method of claim 6, wherein the minimum duration depends on duration of the triggering cycle.

8. The method of claim 6, further comprising:
   calculating a number of no-motion regions and their respective start and end times from the tag-vector and;
   saving the number of no-motion regions and their respective start and end times as timing data.

9. A system for determining time periods of minimal motion of a physiologic organ relative to a trigger of a physiologic triggering signal and within a triggering cycle, the system comprising:
   a physiologic monitoring device configured to monitor the physiologic triggering signal associated with a patient;
   an MRI scanner configured to use an MM cine pulse sequence to acquire a temporal series of projections across a region of interest comprising an organ of interest; and
   a data processor configured to analyze the temporal series of projections to determine one or more times relative to a trigger provided by the physiologic triggering signal during which motion of the organ of interest is below a predefined threshold, wherein motion of the organ of interest is assessed by a process comprising:
   (a) creating a signal intensity versus time curve of one pixel or an average of multiple pixels included in the temporal series of projections,
   (b) applying a noise filter and normalization to the signal intensity versus time curve to yield a filtered and normalized time curve,
   (c) determining the temporal derivative of the filtered and normalized time curve to yield a motion-analog function,
   (d) evaluating the absolute value of the motion-analog function for being smaller than the predefined threshold to determine the one or more times, and
   (e) tagging elements for which an absolute value of the derivative is below a predefined threshold as having no motion in a tag-vector comprising a same number of elements as a motion-analog function.

10. The system of claim 9, wherein the triggering cycle is an RR-interval.

11. The system of claim 9, wherein the physiologic triggering signal is an electrocardiogram.

12. The system of claim 9, wherein the physiologic triggering signal is a pulse oximetry signal.

13. The system of claim 9, wherein the physiologic triggering signal is an acoustic heart signal.

14. The system of claim 9, wherein the physiologic triggering signal is a respiratory signal.

15. The system of claim 9, wherein the physiologic organ is a heart.

16. The system of claim 9, wherein the MRI cine pulse sequence is a steady state free precession (SSFP) sequence.

17. The system of claim 9, wherein the MRI cine pulse sequence is a gradient echo (GRE) sequence.

18. The system of claim 9, wherein the series of projections comprises two orthogonal projections acquired in alternating manner.

19. The system of claim 9, wherein the series of projections comprises three orthogonal projections acquired in alternating manner.

20. The system of claim 9, wherein the MRI cine pulse sequence is prospectively triggered.

21. The system of claim 9, wherein the MRI cine pulse sequence is retrospectively gated.

22. A computer-readable, non-transitory medium holding computer-executable instructions for performing a method for determining time periods of minimal motion of a physiologic organ relative to a trigger of a physiologic triggering signal and within a triggering cycle comprising:
   using an MRI cine pulse sequence to acquire a temporal series of projections across a region of interest comprising an organ of interest; and
   analyzing the temporal series of projections to determine one or more times relative to a trigger provided by the physiologic triggering signal during which motion of the organ of interest is below a predefined threshold, wherein motion of the organ of interest is assessed by a process comprising:
(a) creating a signal intensity versus time curve of one pixel or an average of multiple pixels included in the temporal series of projections,
(b) applying a noise filter and normalization to the signal intensity versus time curve to yield a filtered and normalized time curve,
(c) determining the temporal derivative of the filtered and normalized time curve to yield a motion-analog function,
(d) evaluating the absolute value of the motion-analog function for being smaller than the predefined threshold to determine the one or more times, and
(e) tagging elements for which an absolute value of the derivative is below a predefined threshold as having no motion in a tag-vector comprising a same number of elements as a motion-analog function.

* * * * *